United States Patent
Pulé et al.

(10) Patent No.: US 10,604,570 B2
(45) Date of Patent: *Mar. 31, 2020

(54) CHIMERIC ANTIGEN RECEPTOR SIGNALLING SYSTEM COMPRISING HETERODIMERIZATION DOMAINS

(71) Applicant: UCL BUSINESS PLC, London (GB)

(72) Inventors: Martin Pulé, London (GB); Shaun Cordoba, London (GB)

(73) Assignee: UCL BUSINESS LTD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/548,340

(22) PCT Filed: Feb. 4, 2016

(86) PCT No.: PCT/GB2016/050257
§ 371 (c)(1),
(2) Date: Aug. 2, 2017

(87) PCT Pub. No.: WO2016/124930
PCT Pub. Date: Aug. 11, 2016

(65) Prior Publication Data
US 2018/0016335 A1    Jan. 18, 2018

(30) Foreign Application Priority Data

Feb. 5, 2015  (GB) .................................. 1501936.7

(51) Int. Cl.
| | | |
|---|---|---|
| *C07K 16/28* | (2006.01) | |
| *A61K 35/17* | (2015.01) | |
| *C07K 14/705* | (2006.01) | |
| *A61K 39/00* | (2006.01) | |
| *C12N 5/0783* | (2010.01) | |
| *C07K 14/47* | (2006.01) | |
| *C07K 14/725* | (2006.01) | |
| *C07K 14/73* | (2006.01) | |
| *C12N 7/00* | (2006.01) | |

(52) U.S. Cl.
CPC .......... *C07K 16/2803* (2013.01); *A61K 35/17* (2013.01); *A61K 39/0011* (2013.01); *C07K 14/4702* (2013.01); *C07K 14/705* (2013.01); *C07K 14/7051* (2013.01); *C07K 14/70503* (2013.01); *C07K 14/70514* (2013.01); *C12N 5/0636* (2013.01); *C12N 7/00* (2013.01); *A61K 2039/5156* (2013.01); *C07K 2317/622* (2013.01); *C07K 2319/02* (2013.01); *C07K 2319/03* (2013.01); *C07K 2319/70* (2013.01); *C07K 2319/73* (2013.01); *C12N 2510/00* (2013.01); *C12N 2740/10043* (2013.01)

(58) Field of Classification Search
None
See application file for complete search history.

(56) References Cited

U.S. PATENT DOCUMENTS

| | | | |
|---|---|---|---|
| 2013/0280285 A1* | 10/2013 | Schonfeld .......... | C07K 14/7051 424/185.1 |
| 2016/0311907 A1 | 10/2016 | Brogdon et al. | |
| 2017/0014508 A1 | 1/2017 | Pule et al. | |
| 2017/0081411 A1 | 3/2017 | Engels et al. | |
| 2017/0260269 A1 | 9/2017 | Pule et al. | |
| 2018/0042963 A1 | 2/2018 | Wu et al. | |
| 2018/0050065 A1* | 2/2018 | Pule ...................... | A61K 35/17 |

FOREIGN PATENT DOCUMENTS

| | | |
|---|---|---|
| WO | WO-2014/127261 A1 | 8/2014 |
| WO | WO-2015/142661 A1 | 9/2015 |
| WO | WO-2015/150771 A1 | 10/2015 |
| WO | WO-2016/030691 A1 | 3/2016 |
| WO | WO-2017/137758 A1 | 8/2017 |
| WO | WO-2017/137759 A1 | 8/2017 |
| WO | WO-2017/216562 A1 | 12/2017 |

OTHER PUBLICATIONS

Deyev et al. (Nature Biotechnology Nov. 23, 2003 21 (12): 1486-1492) (Year: 2003).*
Call and Wucherpfenning (Nature Review Immunology Nov. 2007 7:841-850) (Year: 2007).*
Chang et al. (Proc. Natl. Acad. Sci. USA 1994 91: 11408-11412) (Year: 1994).*
Rossi et al. (Bioconjugate Chem. Dec. 14, 2011 23:309-323), (Year: 2011).*
U.S. Appl. No. 15/301,148, filed Sep. 30, 2016.
U.S. Appl. No. 15/506,383, filed Feb. 24, 2017.
Donnelly et al., The 'cleavage' activities of foot-and-mouth disease virus 2A site-directed mutants and naturally occurring '2A-like' sequences. *J. Gen. Virol.* 82: 1027-41 (2001).
Rossi et al., Stably tethered multifunctional structures of defined composition made by the dock and lock method for use in cancer targeting. *Pros. Natl. Acad. Sci. USA*; 103(18): 6841-6 (2006).

(Continued)

*Primary Examiner* — Peter J Reddig
(74) *Attorney, Agent, or Firm* — Marshall, Gerstein & Borun LLP

(57) ABSTRACT

The present invention relates to a chimeric antigen-receptor (CAR) signalling system comprising; (i) a targeting component comprising an antigen-binding domain, a transmembrane domain and a first heterodimerization domain; and (ii) an intracellular signalling component comprising a signalling domain and a second heterodimerization domain; wherein spontaneous heterodimerization between the first and second heterodimerization domains causes the targeting component and signalling component to form a functional CAR complex.

11 Claims, 14 Drawing Sheets

Specification includes a Sequence Listing.

(56) References Cited

OTHER PUBLICATIONS

International Search Report and Written Opinion of ISA dated May 13, 2016, established by European Patent Office for PCT/GB2016/050257, filed Feb. 4, 2016.
Chicaybam et al., A conditional system for the activation of lymphocytes expressing activating and inhibitory CARs, *Hum. Gene Ther.* 21:1418 (2010).
Chicaybam et al., Constuctions and validation of an activating and inhibitory chimeric antigen receptor (Car) system, Cancer Research. 74(Suppl 19):Abstract#2797 (2014).
Clackson et al., Redesigning an FKBP-ligand interface to generate chemical dimerizers with novel specificity, *Proc. Natl. Acad. Sci. USA.* 95:10437-42 (1998).
Gendreizig et al., Induced protein dimerization in vivo through covalent labeling, *J. Am. Chem. Soc.* 125:14970-1 (2003).
Jensen et al., Design and implementation of adoptive therapy with chimeric antigen receptor-modified T cells, Immunol. Rev. 257:127-44 (2014).
Lanitis et al., Chimeric antigen receptor T Cells with dissociated signaling domains exhibit focused antitumor activity with reduced potential for toxicity in vivo, *Cancer Immunol. Res.* 1:43-53 (2013).
White et al., Protein-protein interactions as targets for small-molecule therapeutics in cancer, *Expert Rev. Mol. Med.* 10:e8 (2008).

\* cited by examiner

>Acid/Base ZipCAR (SEQ ID NO: 34)

AQLEKELQALEKENAQLEWELQALEKELAQSGGGGSADAPAYQQGQNQLYNELNLGREEYDVLDKRRGRDPEMGGKPRRKNPQEG
LYNELQKDKMAEAYSEIGMKGERRRGKGHDGLYQGLSTATKDTYDALHMQALPPRRAEGRGSLLTCGDVEENPGPMAVPTQVLGLL
LLMLTDARCDIQMTQSPSSLSASVGDRVTITCRASEDIYFNLVWYQQKPGKAPKLLIYDTNRLADGVPSRFSGSGSGTQYTLTISS
LQPEDFATYCQHYKNYPLTFGQGTKLEIKRSGGGGSGGGGSGGGGSREVQLVESGGGLVQPGGSLRLSCAASGFTLSNYGMHWI
RQAPGKGLEWVSSISLNGGSTYYRDSVKGRFTISRDNAKSTLYLQMNSLRAEDTAVYYCAAQDAYTGGYFDYWGQGTLVTVSSMPC
PAPPVAGPSVFLFPPKPKDTLMIARTPEVTCVVVDVSHEDPEVKFNWYVDGVEVHNAKTKPREEQYNSTYRVVSVLTVLHQDWLNG
KEYKCKVSNKALPAPIEKTISKAKPCPAPPVAGPSVFLFPPKPKDTLMIARTPEVTCVVVDVSHEDPEVKFNWYVDGVEVHNAKTK
PREEQYNSTYRVVSVLTVLHQDWLNGKEYKCKVSNKALPAPIEKTISKAKMALIVLGGVAGLLLFIGLGIFFMALIVLGGVAGLLL
FIGLGIFFCVRCRHRRRSGGGGSAQLEKKLQALKKKLAQLKWKLQALKKKLAQ

>Acid/Base ZipCAR Control (SEQ ID NO: 35)

ADAPAYQQGQNQLYNELNLGREEYDVLDKRRGRDPEMGGKPRRKNPQEGLYNELQKDKMAEAYSEIGMKGERRRGKGHDGLYQGL
STATKDTYDALHMQALPPRRAEGRGSLLTCGDVEENPGPMAVPTQVLGLLLLMLTDARCDIQMTQSPSSLSASVGDRVTITCRASE
DIYFNLVWYQQKPGKAPKLLIYDTNRLADGVPSRFSGSGSGTQYTLTISSLQPEDFATYCQHYKNYPLTFGQGTKLEIKRSGGGG
SGGGGSGGGGSREVQLVESGGGLVQPGGSLRLSCAASGFTLSNYGMHWIRQAPGKGLEWVSSISLNGGSTYYRDSVKGRFTISRD
NAKSTLYLQMNSLRAEDTAVYYCAAQDAYTGGYFDYWGQGTLVTVSSMPCPAPPVAGPSVFLFPPKPKDTLMIARTPEVTCVVVDV
SHEDPEVKFNWYVDGVEVHNAKTKPREEQYNSTYRVVSVLTVLHQDWLNGKEYKCKVSNKALPAPIEKTISKAKPCPAPPVAGPSV
FLFPPKPKDTLMIARTPEVTCVVVDVSHEDPEVKFNWYVDGVEVHNAKTKPREEQYNSTYRVVSVLTVLHQDWLNGKEYKCKVSNK
ALPAPIEKTISKAKMALIVLGGVAGLLLFIGLGIFFCVRCRHRRRSGGGGSAQLEKKLQALKKK
NAQLKWKLQALKKKLAQ

FIG. 11

>DDD1/AD1 ZipCAR (SEQ ID NO: 36)
VQIEYLAKQIVDNAIQQASGGGGSADAPAYQQGQNQLYNELNLGREEYDVLDKRRGRDPEMGGKPRRKNPQEGLYNELQKDKMAE
AYSEIGMKGERRRGKHDGLYQGLSTATKDTYDALHMQALPPRRAEGRGSLLTCGDVEENPGPMAVPTQVLGLLLLWLTDARCDIQ
MTQSPSSLSASVGDRVTITCRASEDIYFNLVWYQQKPGKAPKLLIYDTNRLADGVPSRFSGSGSGTQYTLTISSLQPEDFATYYCQ
HYKNYPLTFGQGTKLEIKRSGGGGSGGGGSGGGGSRSEVQLVESGGGLVQPGSLRLSCAASGFTLSNYGMHWIRQAPGKGLEWVS
SISLNGGSTYYRDSVKGRFTISRDNAKSTLYLQMNSLRAEDTAVYYCAAQDAYTGGYFDYWGQGTLVTVSSMPCPAPPVAGPSVFL
FPPKPKDTLMIARTPEVTCVVVDVSHEDPEVKFNWYVDGVEVHNAKTKPREEQYNSTYRVVSVLTVLHQDWLNGKEYKCKVSNKAL
PAPIEKTISKAKPCPAPPVAGPSVFLFPPKPKDTLMIARTPEVTCVVVDVSHEDPEVKFNWYVDGVEVHNAKTKPREEQYNSTYRV
VSVLTVLHQDWLNGKEYKCKVSNKALPAPIEKTISKAKMALIVLGGVAGLLLFIGLGIFFMALIVLGGVAGLLLFIGLGIFFCVRC
RHRRSGGGGSHIQIPPGLTELLQGYTVEVLRQQPPDLVEFAVEYFTRLREARA

>DDD1/AD1 ZipCAR control (SEQ ID NO: 37)
ADAPAYQQGQNQLYNELNLGREEYDVLDKRRGRDPEMGGKPRRKNPQEGLYNELQKDKMAEEAYSEIGMKGERRRGKGHDGLYQGL
STATKDTYDALHMQALPPRRAEGRGSLLTCGDVEENPGPMAVPTQVLGLLLLWLTDARCDIQMTQSPSSLSASVGDRVTITCRASE
DIYFNLVWYQQKPGKAPKLLIYDTNRLADGVPSRFSGSGSGTQYTLTISSLQPEDFATYYCQHYKNYPLTFGQGTKLEIKRSGGGG
SGGGGSGGGGSRSEVQLVESGGGLVQPGSLRLSCAASGFTLSNYGMHWIRQAPGKGLEWVSSISLNGGSTYYRDSVKGRFTISRD
NAKSTLYLQMNSLRAEDTAVYYCAAQDAYTGGYFDWGQGTLVTVSSVLTVLHQDWLNGKEYKCKVSNKALPAPIEKTISKAKPCPAPPVAGPSV
SHEDPEVKFNWYVDGVEVHNAKTKPREEQYNSTYRVVSVLTVLHQDWLNGKEYKCKVSNKALPAPIEKTISKAKPCPAPPVAGPSV
FLFPPKPKDTLMIARTPEVTCVVVDVSHEDPEVKFNWYVDGVEVHNAKTKPREEQYNSTYRVVSVLTVLHQDWLNGKEYKCKVSNK
ALPAPIEKTISKAKMALIVLGGVAGLLLFIGLGIFFCVRCRHRRRSGGGGSSHIQIPPGLTELL
QGYTVEVLRQQPPDLVEFAVEYFTRLREARA FIG. 11 (Continued)

SEQUENCE LISTING

```
<160> NUMBER OF SEQ ID NOS: 37

<210> SEQ ID NO 1
<211> LENGTH: 29
<212> TYPE: PRT
<213> ORGANISM: Artificial Sequence
<220> FEATURE:
<223> OTHER INFORMATION: Heterodimerization domain

<400> SEQUENCE: 1

Gln Leu Glu Lys Glu Leu Gln Ala Leu Glu Lys Glu Asn Ala Gln Leu
1               5                   10                  15

Glu Trp Glu Leu Gln Ala Leu Glu Lys Glu Leu Ala Gln
            20                  25

<210> SEQ ID NO 2
<211> LENGTH: 29
<212> TYPE: PRT
<213> ORGANISM: Artificial Sequence
<220> FEATURE:
<223> OTHER INFORMATION: Heterodimerization domain

<400> SEQUENCE: 2

Gln Leu Glu Lys Lys Leu Gln Ala Leu Lys Lys Lys Asn Ala Gln Leu
1               5                   10                  15

Lys Trp Lys Leu Gln Ala Leu Lys Lys Lys Leu Ala Gln
            20                  25

<210> SEQ ID NO 3
<211> LENGTH: 44
<212> TYPE: PRT
<213> ORGANISM: Artificial Sequence
<220> FEATURE:
<223> OTHER INFORMATION: Dimerisation and docking domain (DDD1)

<400> SEQUENCE: 3

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 4
<211> LENGTH: 18
<212> TYPE: PRT
<213> ORGANISM: Artificial Sequence
<220> FEATURE:
<223> OTHER INFORMATION: Anchoring domain (AD1)

<400> SEQUENCE: 4

Val Gln Ile Glu Tyr Leu Ala Lys Gln Ile Val Asp Asn Ala Ile Gln
1               5                   10                  15

Gln Ala
```

```
<210> SEQ ID NO 5
<211> LENGTH: 21
<212> TYPE: PRT
<213> ORGANISM: Artificial Sequence
<220> FEATURE:
<223> OTHER INFORMATION: Signal peptide

<400> SEQUENCE: 5

Met Gly Thr Ser Leu Leu Cys Trp Met Ala Leu Cys Leu Leu Gly Ala
1               5                   10                  15

Asp His Ala Asp Gly
            20

<210> SEQ ID NO 6
<211> LENGTH: 21
<212> TYPE: PRT
<213> ORGANISM: Artificial Sequence
<220> FEATURE:
<223> OTHER INFORMATION: Signal peptide

<400> SEQUENCE: 6

Met Ser Leu Pro Val Thr Ala Leu Leu Leu Pro Leu Ala Leu Leu Leu
1               5                   10                  15

His Ala Ala Arg Pro
            20

<210> SEQ ID NO 7
<211> LENGTH: 20
<212> TYPE: PRT
<213> ORGANISM: Artificial Sequence
<220> FEATURE:
<223> OTHER INFORMATION: Signal peptide

<400> SEQUENCE: 7

Met Ala Val Pro Thr Gln Val Leu Gly Leu Leu Leu Leu Trp Leu Thr
1               5                   10                  15

Asp Ala Arg Cys
            20

<210> SEQ ID NO 8
<211> LENGTH: 234
<212> TYPE: PRT
<213> ORGANISM: Artificial Sequence
<220> FEATURE:
<223> OTHER INFORMATION: hinge-CH2CH3 of human IgG1

<400> SEQUENCE: 8

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 9
<211> LENGTH: 46
<212> TYPE: PRT
<213> ORGANISM: Artificial Sequence
<220> FEATURE:
<223> OTHER INFORMATION: human CD8 stalk

<400> SEQUENCE: 9

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 10
<211> LENGTH: 20
<212> TYPE: PRT
<213> ORGANISM: Artificial Sequence
<220> FEATURE:
<223> OTHER INFORMATION: human IgG1 hinge

<400> SEQUENCE: 10

Ala Glu Pro Lys Ser Pro Asp Lys Thr His Thr Cys Pro Pro Cys Pro
1               5                   10                  15

Lys Asp Pro Lys
            20

<210> SEQ ID NO 11
<211> LENGTH: 185
<212> TYPE: PRT
<213> ORGANISM: Artificial Sequence
<220> FEATURE:
<223> OTHER INFORMATION: CD2 ectodomain

<400> SEQUENCE: 11

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
                20                  25                  30

Ile Lys Trp Glu Lys Thr Ser Asp Lys Lys Ile Ala Gln Phe Arg
            35                  40                  45

Lys Glu Lys Glu Thr Phe Lys Glu Lys Asp Thr Tyr Lys Leu Phe Lys

```
            50                  55                  60
Asn Gly Thr Leu Lys Ile Lys His Leu Lys Thr Asp Gln Asp Ile
 65                  70                  75                  80

Tyr Lys Val Ser Ile Tyr Asp Thr Lys Gly Lys Asn Val Leu Glu Lys
                 85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
            115                 120                 125

Asp Pro Glu Leu Asn Leu Tyr Gln Asp Gly Lys His Leu Lys Leu Ser
130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185

<210> SEQ ID NO 12
<211> LENGTH: 259
<212> TYPE: PRT
<213> ORGANISM: Artificial Sequence
<220> FEATURE:
<223> OTHER INFORMATION: CD34 ectodomain

<400> SEQUENCE: 12

Ser Leu Asp Asn Asn Gly Thr Ala Thr Pro Glu Leu Pro Thr Gln Gly
 1               5                  10                  15

Thr Phe Ser Asn Val Ser Thr Asn Val Ser Tyr Gln Glu Thr Thr Thr
                20                  25                  30

Pro Ser Thr Leu Gly Ser Thr Ser Leu His Pro Val Ser Gln His Gly
            35                  40                  45

Asn Glu Ala Thr Thr Asn Ile Thr Glu Thr Thr Val Lys Phe Thr Ser
 50                  55                  60

Thr Ser Val Ile Thr Ser Val Tyr Gly Asn Thr Asn Ser Ser Val Gln
65                  70                  75                  80

Ser Gln Thr Ser Val Ile Ser Thr Val Phe Thr Thr Pro Ala Asn Val
                85                  90                  95

Ser Thr Pro Glu Thr Thr Leu Lys Pro Ser Leu Ser Pro Gly Asn Val
            100                 105                 110

Ser Asp Leu Ser Thr Thr Ser Thr Ser Leu Ala Thr Ser Pro Thr Lys
            115                 120                 125

Pro Tyr Thr Ser Ser Pro Ile Leu Ser Asp Ile Lys Ala Glu Ile
130                 135                 140

Lys Cys Ser Gly Ile Arg Glu Val Lys Leu Thr Gln Gly Ile Cys Leu
145                 150                 155                 160

Glu Gln Asn Lys Thr Ser Ser Cys Ala Glu Phe Lys Lys Asp Arg Gly
                165                 170                 175

Glu Gly Leu Ala Arg Val Leu Cys Gly Glu Glu Gln Ala Asp Ala Asp
            180                 185                 190

Ala Gly Ala Gln Val Cys Ser Leu Leu Leu Ala Gln Ser Glu Val Arg
            195                 200                 205

Pro Gln Cys Leu Leu Leu Val Leu Ala Asn Arg Thr Glu Ile Ser Ser
210                 215                 220

Lys Leu Gln Leu Met Lys Lys His Gln Ser Asp Leu Lys Lys Leu Gly
```

```
                225                 230                 235                 240
Ile Leu Asp Phe Thr Glu Gln Asp Val Ala Ser His Gln Ser Tyr Ser
                    245                 250                 255

Gln Lys Thr

<210> SEQ ID NO 13
<211> LENGTH: 112
<212> TYPE: PRT
<213> ORGANISM: Artificial Sequence
<220> FEATURE:
<223> OTHER INFORMATION: CD3 Z endodomain

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 14
<211> LENGTH: 152
<212> TYPE: PRT
<213> ORGANISM: Artificial Sequence
<220> FEATURE:
<223> OTHER INFORMATION: CD28 and CD3 Zeta endodomains

<400> SEQUENCE: 14

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
                20                  25                  30

Arg Asp Phe Ala Ala Tyr Arg Ser Arg Val Lys Phe Ser Arg Ser Ala
            35                  40                  45

Asp Ala Pro Ala Tyr Gln Gln Gly Gln Asn Gln Leu Tyr Asn Glu Leu
    50                  55                  60

Asn Leu Gly Arg Arg Glu Glu Tyr Asp Val Leu Asp Lys Arg Arg Gly
65                  70                  75                  80

Arg Asp Pro Glu Met Gly Gly Lys Pro Arg Arg Lys Asn Pro Gln Glu
                85                  90                  95

Gly Leu Tyr Asn Glu Leu Gln Lys Asp Lys Met Ala Glu Ala Tyr Ser
                100                 105                 110

Glu Ile Gly Met Lys Gly Glu Arg Arg Arg Gly Lys Gly His Asp Gly
            115                 120                 125

Leu Tyr Gln Gly Leu Ser Thr Ala Thr Lys Asp Thr Tyr Asp Ala Leu
    130                 135                 140

His Met Gln Ala Leu Pro Pro Arg
145                 150
```

```
<210> SEQ ID NO 15
<211> LENGTH: 188
<212> TYPE: PRT
<213> ORGANISM: Artificial Sequence
<220> FEATURE:
<223> OTHER INFORMATION: CD28, OX40 and CD3 Zeta endodomains

<400> SEQUENCE: 15

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
        35                  40                  45

Ala His Lys Pro Pro Gly Gly Gly Ser Phe Arg Thr Pro Ile Gln Glu
    50                  55                  60

Glu Gln Ala Asp Ala His Ser Thr Leu Ala Lys Ile Arg Val Lys Phe
65                  70                  75                  80

Ser Arg Ser Ala Asp Ala Pro Ala Tyr Gln Gln Gly Gln Asn Gln Leu
                85                  90                  95

Tyr Asn Glu Leu Asn Leu Gly Arg Arg Glu Glu Tyr Asp Val Leu Asp
            100                 105                 110

Lys Arg Arg Gly Arg Asp Pro Glu Met Gly Gly Lys Pro Arg Arg Lys
        115                 120                 125

Asn Pro Gln Glu Gly Leu Tyr Asn Glu Leu Gln Lys Asp Lys Met Ala
    130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
            180                 185

<210> SEQ ID NO 16
<211> LENGTH: 38
<212> TYPE: PRT
<213> ORGANISM: Artificial Sequence
<220> FEATURE:
<223> OTHER INFORMATION: ICOS endodomain

<400> SEQUENCE: 16

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 17
<211> LENGTH: 48
<212> TYPE: PRT
<213> ORGANISM: Artificial Sequence
<220> FEATURE:
<223> OTHER INFORMATION: CD27 endodomain

<400> SEQUENCE: 17

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30
```

```
Ile Pro Ile Gln Glu Asp Tyr Arg Lys Pro Glu Pro Ala Cys Ser Pro
        35                  40                  45
```

<210> SEQ ID NO 18
<211> LENGTH: 111
<212> TYPE: PRT
<213> ORGANISM: Artificial Sequence
<220> FEATURE:
<223> OTHER INFORMATION: BTLA endodomain

<400> SEQUENCE: 18

```
Arg Arg His Gln Gly Lys Gln Asn Glu Leu Ser Asp Thr Ala Gly Arg
1               5                   10                  15

Glu Ile Asn Leu Val Asp Ala His Leu Lys Ser Glu Gln Thr Glu Ala
            20                  25                  30

Ser Thr Arg Gln Asn Ser Gln Val Leu Leu Ser Glu Thr Gly Ile Tyr
        35                  40                  45

Asp Asn Asp Pro Asp Leu Cys Phe Arg Met Gln Glu Gly Ser Glu Val
    50                  55                  60

Tyr Ser Asn Pro Cys Leu Glu Glu Asn Lys Pro Gly Ile Val Tyr Ala
65                  70                  75                  80

Ser Leu Asn His Ser Val Ile Gly Pro Asn Ser Arg Leu Ala Arg Asn
                85                  90                  95

Val Lys Glu Ala Pro Thr Glu Tyr Ala Ser Ile Cys Val Arg Ser
            100                 105                 110
```

<210> SEQ ID NO 19
<211> LENGTH: 188
<212> TYPE: PRT
<213> ORGANISM: Artificial Sequence
<220> FEATURE:
<223> OTHER INFORMATION: CD30 endodomain

<400> SEQUENCE: 19

```
His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
            20                  25                  30

Pro Arg Arg Ser Ser Thr Gln Leu Arg Ser Gly Ala Ser Val Thr Glu
        35                  40                  45

Pro Val Ala Glu Glu Arg Gly Leu Met Ser Gln Pro Leu Met Glu Thr
    50                  55                  60

Cys His Ser Val Gly Ala Ala Tyr Leu Glu Ser Leu Pro Leu Gln Asp
65                  70                  75                  80

Ala Ser Pro Ala Gly Gly Pro Ser Ser Pro Arg Asp Leu Pro Glu Pro
                85                  90                  95

Arg Val Ser Thr Glu His Thr Asn Asn Lys Ile Glu Lys Ile Tyr Ile
            100                 105                 110

Met Lys Ala Asp Thr Val Ile Val Gly Thr Val Lys Ala Glu Leu Pro
        115                 120                 125

Glu Gly Arg Gly Leu Ala Gly Pro Ala Glu Pro Glu Leu Glu Glu Glu
    130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185
```

```
                       180                 185

<210> SEQ ID NO 20
<211> LENGTH: 58
<212> TYPE: PRT
<213> ORGANISM: Artificial Sequence
<220> FEATURE:
<223> OTHER INFORMATION: GITR endodomain

<400> SEQUENCE: 20

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55

<210> SEQ ID NO 21
<211> LENGTH: 60
<212> TYPE: PRT
<213> ORGANISM: Artificial Sequence
<220> FEATURE:
<223> OTHER INFORMATION: HVEM endodomain

<400> SEQUENCE: 21

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 22
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 22

Tyr His Ala Asp Tyr Tyr Lys Gln Arg Leu Ile His Asp Val Glu Met
1               5                   10                  15

Asn Pro Gly Pro
            20

<210> SEQ ID NO 23
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 23

His Tyr Ala Gly Tyr Phe Ala Asp Leu Leu Ile His Asp Ile Glu Thr
1               5                   10                  15

Asn Pro Gly Pro
            20
```

```
<210> SEQ ID NO 24
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 24

Gln Cys Thr Asn Tyr Ala Leu Leu Lys Leu Ala Gly Asp Val Glu Ser
1               5                   10                  15

Asn Pro Gly Pro
            20

<210> SEQ ID NO 25
<211> LENGTH: 19
<212> TYPE: PRT
<213> ORGANISM: Artificial Sequence
<220> FEATURE:
<223> OTHER INFORMATION: 2A-like self-cleaving peptide

<400> SEQUENCE: 25

Ala Thr Asn Phe Ser Leu Leu Lys Gln Ala Gly Asp Val Glu Glu Asn
1               5                   10                  15

Pro Gly Pro

<210> SEQ ID NO 26
<211> LENGTH: 19
<212> TYPE: PRT
<213> ORGANISM: Artificial Sequence
<220> FEATURE:
<223> OTHER INFORMATION: 2A-like self-cleaving peptide

<400> SEQUENCE: 26

Ala Ala Arg Gln Met Leu Leu Leu Leu Ser Gly Asp Val Glu Thr Asn
1               5                   10                  15

Pro Gly Pro

<210> SEQ ID NO 27
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 27

Arg Ala Glu Gly Arg Gly Ser Leu Leu Thr Cys Gly Asp Val Glu Glu
1               5                   10                  15

Asn Pro Gly Pro
            20

<210> SEQ ID NO 28
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 28

Thr Arg Ala Glu Ile Glu Asp Glu Leu Ile Arg Ala Gly Ile Glu Ser
1               5                   10                  15

Asn Pro Gly Pro
            20

<210> SEQ ID NO 29
```

```
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 29

Thr Arg Ala Glu Ile Glu Asp Glu Leu Ile Arg Ala Asp Ile Glu Ser
1               5                   10                  15

Asn Pro Gly Pro
            20

<210> SEQ ID NO 30
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 30

Ala Lys Phe Gln Ile Asp Lys Ile Leu Ile Ser Gly Asp Val Glu Leu
1               5                   10                  15

Asn Pro Gly Pro
            20

<210> SEQ ID NO 31
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 31

Ser Ser Ile Ile Arg Thr Lys Met Leu Val Ser Gly Asp Val Glu Glu
1               5                   10                  15

Asn Pro Gly Pro
            20

<210> SEQ ID NO 32
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 32

Cys Asp Ala Gln Arg Gln Lys Leu Leu Leu Ser Gly Asp Ile Glu Gln
1               5                   10                  15

Asn Pro Gly Pro
            20

<210> SEQ ID NO 33
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 33

Tyr Pro Ile Asp Phe Gly Gly Phe Leu Val Lys Ala Asp Ser Glu Phe
1               5                   10                  15

Asn Pro Gly Pro
            20
```

<210> SEQ ID NO 34
<211> LENGTH: 741
<212> TYPE: PRT
<213> ORGANISM: Artificial Sequence
<220> FEATURE:
<223> OTHER INFORMATION: Acid/Base Leucine zipper zipCAR

<400> SEQUENCE: 34

```
Ala Gln Leu Glu Lys Glu Leu Gln Ala Leu Glu Lys Glu Asn Ala Gln
1               5                   10                  15

Leu Glu Trp Glu Leu Gln Ala Leu Glu Lys Glu Leu Ala Gln Ser Gly
            20                  25                  30

Gly Gly Gly Ser Ala Asp Ala Pro Ala Tyr Gln Gln Gly Gln Asn Gln
        35                  40                  45

Leu Tyr Asn Glu Leu Asn Leu Gly Arg Arg Glu Glu Tyr Asp Val Leu
50                  55                  60

Asp Lys Arg Arg Gly Arg Asp Pro Glu Met Gly Gly Lys Pro Arg Arg
65                  70                  75                  80

Lys Asn Pro Gln Glu Gly Leu Tyr Asn Glu Leu Gln Lys Asp Lys Met
                85                  90                  95

Ala Glu Ala Tyr Ser Glu Ile Gly Met Lys Gly Glu Arg Arg Arg Gly
            100                 105                 110

Lys Gly His Asp Gly Leu Tyr Gln Gly Leu Ser Thr Ala Thr Lys Asp
        115                 120                 125

Thr Tyr Asp Ala Leu His Met Gln Ala Leu Pro Pro Arg Arg Ala Glu
130                 135                 140

Gly Arg Gly Ser Leu Leu Thr Cys Gly Asp Val Glu Glu Asn Pro Gly
145                 150                 155                 160

Pro Met Ala Val Pro Thr Gln Val Leu Gly Leu Leu Leu Leu Trp Leu
                165                 170                 175

Thr Asp Ala Arg Cys Asp Ile Gln Met Thr Gln Ser Pro Ser Ser Leu
            180                 185                 190

Ser Ala Ser Val Gly Asp Arg Val Thr Ile Thr Cys Arg Ala Ser Glu
        195                 200                 205

Asp Ile Tyr Phe Asn Leu Val Trp Tyr Gln Gln Lys Pro Gly Lys Ala
210                 215                 220

Pro Lys Leu Leu Ile Tyr Asp Thr Asn Arg Leu Ala Asp Gly Val Pro
225                 230                 235                 240

Ser Arg Phe Ser Gly Ser Gly Ser Gly Thr Gln Tyr Thr Leu Thr Ile
                245                 250                 255

Ser Ser Leu Gln Pro Glu Asp Phe Ala Thr Tyr Tyr Cys Gln His Tyr
            260                 265                 270

Lys Asn Tyr Pro Leu Thr Phe Gly Gln Gly Thr Lys Leu Glu Ile Lys
        275                 280                 285

Arg Ser Gly Gly Gly Gly Ser Gly Gly Gly Gly Ser Gly Gly Gly Gly
290                 295                 300

Ser Arg Ser Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Leu
                325                 330                 335

Ser Asn Tyr Gly Met His Trp Ile Arg Gln Ala Pro Gly Lys Gly Leu
            340                 345                 350

Glu Trp Val Ser Ser Ile Ser Leu Asn Gly Gly Ser Thr Tyr Tyr Arg
        355                 360                 365

Asp Ser Val Lys Gly Arg Phe Thr Ile Ser Arg Asp Asn Ala Lys Ser
```

```
                370             375             380
Thr Leu Tyr Leu Gln Met Asn Ser Leu Arg Ala Glu Asp Thr Ala Val
385                 390                 395                 400

Tyr Tyr Cys Ala Ala Gln Asp Ala Tyr Thr Gly Gly Tyr Phe Asp Tyr
                405                 410                 415

Trp Gly Gln Gly Thr Leu Val Thr Val Ser Ser Met Pro Cys Pro Ala
            420                 425                 430

Pro Pro Val Ala Gly Pro Ser Val Phe Leu Phe Pro Pro Lys Pro Lys
        435                 440                 445

Asp Thr Leu Met Ile Ala Arg Thr Pro Glu Val Thr Cys Val Val Val
    450                 455                 460

Asp Val Ser His Glu Asp Pro Glu Val Lys Phe Asn Trp Tyr Val Asp
465                 470                 475                 480

Gly Val Glu Val His Asn Ala Lys Thr Lys Pro Arg Glu Glu Gln Tyr
                485                 490                 495

Asn Ser Thr Tyr Arg Val Val Ser Val Leu Thr Val Leu His Gln Asp
            500                 505                 510

Trp Leu Asn Gly Lys Glu Tyr Lys Cys Lys Val Ser Asn Lys Ala Leu
        515                 520                 525

Pro Ala Pro Ile Glu Lys Thr Ile Ser Lys Ala Lys Pro Cys Pro Ala
    530                 535                 540

Pro Pro Val Ala Gly Pro Ser Val Phe Leu Phe Pro Pro Lys Pro Lys
545                 550                 555                 560

Asp Thr Leu Met Ile Ala Arg Thr Pro Glu Val Thr Cys Val Val Val
                565                 570                 575

Asp Val Ser His Glu Asp Pro Glu Val Lys Phe Asn Trp Tyr Val Asp
            580                 585                 590

Gly Val Glu Val His Asn Ala Lys Thr Lys Pro Arg Glu Glu Gln Tyr
        595                 600                 605

Asn Ser Thr Tyr Arg Val Val Ser Val Leu Thr Val Leu His Gln Asp
    610                 615                 620

Trp Leu Asn Gly Lys Glu Tyr Lys Cys Lys Val Ser Asn Lys Ala Leu
625                 630                 635                 640

Pro Ala Pro Ile Glu Lys Thr Ile Ser Lys Ala Lys Met Ala Leu Ile
                645                 650                 655

Val Leu Gly Gly Val Ala Gly Leu Leu Leu Phe Ile Gly Leu Gly Ile
            660                 665                 670

Phe Phe Met Ala Leu Ile Val Leu Gly Gly Val Ala Gly Leu Leu Leu
        675                 680                 685

Phe Ile Gly Leu Gly Ile Phe Phe Cys Val Arg Cys Arg His Arg Arg
    690                 695                 700

Arg Ser Gly Gly Gly Gly Ser Ala Gln Leu Glu Lys Leu Gln Ala
705                 710                 715                 720

Leu Lys Lys Lys Asn Ala Gln Leu Lys Trp Lys Leu Gln Ala Leu Lys
                725                 730                 735

Lys Lys Leu Ala Gln
            740

<210> SEQ ID NO 35
<211> LENGTH: 705
<212> TYPE: PRT
<213> ORGANISM: Artificial Sequence
<220> FEATURE:
<223> OTHER INFORMATION: Acid/Base Leucine zipper zipCAR Control
```

```
<400> SEQUENCE: 35

Ala Asp Ala Pro Ala Tyr Gln Gln Gly Gln Asn Gln Leu Tyr Asn Glu
1               5                   10                  15

Leu Asn Leu Gly Arg Arg Glu Glu Tyr Asp Val Leu Asp Lys Arg Arg
            20                  25                  30

Gly Arg Asp Pro Glu Met Gly Gly Lys Pro Arg Arg Lys Asn Pro Gln
        35                  40                  45

Glu Gly Leu Tyr Asn Glu Leu Gln Lys Asp Lys Met Ala Glu Ala Tyr
    50                  55                  60

Ser Glu Ile Gly Met Lys Gly Glu Arg Arg Arg Gly Lys Gly His Asp
65                  70                  75                  80

Gly Leu Tyr Gln Gly Leu Ser Thr Ala Thr Lys Asp Thr Tyr Asp Ala
                85                  90                  95

Leu His Met Gln Ala Leu Pro Pro Arg Ala Glu Gly Arg Gly Ser
            100                 105                 110

Leu Leu Thr Cys Gly Asp Val Glu Glu Asn Pro Gly Pro Met Ala Val
        115                 120                 125

Pro Thr Gln Val Leu Gly Leu Leu Leu Leu Trp Leu Thr Asp Ala Arg
130                 135                 140

Cys Asp Ile Gln Met Thr Gln Ser Pro Ser Ser Leu Ser Ala Ser Val
145                 150                 155                 160

Gly Asp Arg Val Thr Ile Thr Cys Arg Ala Ser Glu Asp Ile Tyr Phe
                165                 170                 175

Asn Leu Val Trp Tyr Gln Gln Lys Pro Gly Lys Ala Pro Lys Leu Leu
            180                 185                 190

Ile Tyr Asp Thr Asn Arg Leu Ala Asp Gly Val Pro Ser Arg Phe Ser
        195                 200                 205

Gly Ser Gly Ser Gly Thr Gln Tyr Thr Leu Thr Ile Ser Ser Leu Gln
    210                 215                 220

Pro Glu Asp Phe Ala Thr Tyr Tyr Cys Gln His Tyr Lys Asn Tyr Pro
225                 230                 235                 240

Leu Thr Phe Gly Gln Gly Thr Lys Leu Glu Ile Lys Arg Ser Gly Gly
                245                 250                 255

Gly Gly Ser Gly Gly Gly Gly Ser Gly Gly Gly Ser Arg Ser Glu
            260                 265                 270

Val Gln Leu Val Glu Ser Gly Gly Leu Val Gln Pro Gly Gly Ser
        275                 280                 285

Leu Arg Leu Ser Cys Ala Ala Ser Gly Phe Thr Leu Ser Asn Tyr Gly
    290                 295                 300

Met His Trp Ile Arg Gln Ala Pro Gly Lys Gly Leu Glu Trp Val Ser
305                 310                 315                 320

Ser Ile Ser Leu Asn Gly Gly Ser Thr Tyr Tyr Arg Asp Ser Val Lys
                325                 330                 335

Gly Arg Phe Thr Ile Ser Arg Asp Asn Ala Lys Ser Thr Leu Tyr Leu
            340                 345                 350

Gln Met Asn Ser Leu Arg Ala Glu Asp Thr Ala Val Tyr Tyr Cys Ala
        355                 360                 365

Ala Gln Asp Ala Tyr Thr Gly Gly Tyr Phe Asp Tyr Trp Gly Gln Gly
    370                 375                 380

Thr Leu Val Thr Val Ser Ser Met Pro Cys Pro Ala Pro Pro Val Ala
385                 390                 395                 400

Gly Pro Ser Val Phe Leu Phe Pro Pro Lys Pro Lys Asp Thr Leu Met
                405                 410                 415
```

```
Ile Ala Arg Thr Pro Glu Val Thr Cys Val Val Val Asp Val Ser His
            420                 425                 430
Glu Asp Pro Glu Val Lys Phe Asn Trp Tyr Val Asp Gly Val Glu Val
        435                 440                 445
His Asn Ala Lys Thr Lys Pro Arg Glu Glu Gln Tyr Asn Ser Thr Tyr
    450                 455                 460
Arg Val Val Ser Val Leu Thr Val Leu His Gln Asp Trp Leu Asn Gly
465                 470                 475                 480
Lys Glu Tyr Lys Cys Lys Val Ser Asn Lys Ala Leu Pro Ala Pro Ile
                485                 490                 495
Glu Lys Thr Ile Ser Lys Ala Lys Pro Cys Pro Ala Pro Pro Val Ala
            500                 505                 510
Gly Pro Ser Val Phe Leu Phe Pro Pro Lys Pro Lys Asp Thr Leu Met
        515                 520                 525
Ile Ala Arg Thr Pro Glu Val Thr Cys Val Val Val Asp Val Ser His
    530                 535                 540
Glu Asp Pro Glu Val Lys Phe Asn Trp Tyr Val Asp Gly Val Glu Val
545                 550                 555                 560
His Asn Ala Lys Thr Lys Pro Arg Glu Glu Gln Tyr Asn Ser Thr Tyr
                565                 570                 575
Arg Val Val Ser Val Leu Thr Val Leu His Gln Asp Trp Leu Asn Gly
            580                 585                 590
Lys Glu Tyr Lys Cys Lys Val Ser Asn Lys Ala Leu Pro Ala Pro Ile
        595                 600                 605
Glu Lys Thr Ile Ser Lys Ala Lys Met Ala Leu Ile Val Leu Gly Gly
    610                 615                 620
Val Ala Gly Leu Leu Leu Phe Ile Gly Leu Gly Ile Phe Phe Met Ala
625                 630                 635                 640
Leu Ile Val Leu Gly Gly Val Ala Gly Leu Leu Leu Phe Ile Gly Leu
                645                 650                 655
Gly Ile Phe Phe Cys Val Arg Cys Arg His Arg Arg Ser Gly Gly
            660                 665                 670
Gly Gly Ser Ala Gln Leu Glu Lys Lys Leu Gln Ala Leu Lys Lys Lys
        675                 680                 685
Asn Ala Gln Leu Lys Trp Lys Leu Gln Ala Leu Lys Lys Lys Leu Ala
    690                 695                 700
Gln
705

<210> SEQ ID NO 36
<211> LENGTH: 743
<212> TYPE: PRT
<213> ORGANISM: Artificial Sequence
<220> FEATURE:
<223> OTHER INFORMATION: DDD1/AD1 based zipCAR

<400> SEQUENCE: 36

Val Gln Ile Glu Tyr Leu Ala Lys Gln Ile Val Asp Asn Ala Ile Gln
1               5                   10                  15
Gln Ala Ser Gly Gly Gly Gly Ser Ala Asp Ala Pro Ala Tyr Gln Gln
                20                  25                  30
Gly Gln Asn Gln Leu Tyr Asn Glu Leu Asn Leu Gly Arg Arg Glu Glu
            35                  40                  45
Tyr Asp Val Leu Asp Lys Arg Arg Gly Arg Asp Pro Glu Met Gly Gly
        50                  55                  60
```

Lys Pro Arg Lys Asn Pro Gln Glu Gly Leu Tyr Asn Glu Leu Gln
65                  70                  75                  80

Lys Asp Lys Met Ala Glu Ala Tyr Ser Glu Ile Gly Met Lys Gly Glu
            85                  90                  95

Arg Arg Arg Gly Lys Gly His Asp Gly Leu Tyr Gln Gly Leu Ser Thr
            100                 105                 110

Ala Thr Lys Asp Thr Tyr Asp Ala Leu His Met Gln Ala Leu Pro Pro
            115                 120                 125

Arg Arg Ala Glu Gly Arg Gly Ser Leu Leu Thr Cys Gly Asp Val Glu
130                 135                 140

Glu Asn Pro Gly Pro Met Ala Val Pro Thr Gln Val Leu Gly Leu Leu
145                 150                 155                 160

Leu Leu Trp Leu Thr Asp Ala Arg Cys Asp Ile Gln Met Thr Gln Ser
            165                 170                 175

Pro Ser Ser Leu Ser Ala Ser Val Gly Asp Arg Val Thr Ile Thr Cys
            180                 185                 190

Arg Ala Ser Glu Asp Ile Tyr Phe Asn Leu Val Trp Tyr Gln Gln Lys
            195                 200                 205

Pro Gly Lys Ala Pro Lys Leu Leu Ile Tyr Asp Thr Asn Arg Leu Ala
210                 215                 220

Asp Gly Val Pro Ser Arg Phe Ser Gly Ser Gly Ser Gly Thr Gln Tyr
225                 230                 235                 240

Thr Leu Thr Ile Ser Ser Leu Gln Pro Glu Asp Phe Ala Thr Tyr Tyr
            245                 250                 255

Cys Gln His Tyr Lys Asn Tyr Pro Leu Thr Phe Gly Gln Gly Thr Lys
            260                 265                 270

Leu Glu Ile Lys Arg Ser Gly Gly Gly Ser Gly Gly Gly Gly Ser
            275                 280                 285

Gly Gly Gly Gly Ser Arg Ser Glu Val Gln Leu Val Glu Ser Gly Gly
290                 295                 300

Gly Leu Val Gln Pro Gly Gly Ser Leu Arg Leu Ser Cys Ala Ala Ser
305                 310                 315                 320

Gly Phe Thr Leu Ser Asn Tyr Gly Met His Trp Ile Arg Gln Ala Pro
            325                 330                 335

Gly Lys Gly Leu Glu Trp Val Ser Ser Ile Ser Leu Asn Gly Gly Ser
            340                 345                 350

Thr Tyr Tyr Arg Asp Ser Val Lys Gly Arg Phe Thr Ile Ser Arg Asp
            355                 360                 365

Asn Ala Lys Ser Thr Leu Tyr Leu Gln Met Asn Ser Leu Arg Ala Glu
            370                 375                 380

Asp Thr Ala Val Tyr Tyr Cys Ala Ala Gln Asp Ala Tyr Thr Gly Gly
385                 390                 395                 400

Tyr Phe Asp Tyr Trp Gly Gln Gly Thr Leu Val Thr Val Ser Ser Met
            405                 410                 415

Pro Cys Pro Ala Pro Pro Val Ala Gly Pro Ser Val Phe Leu Phe Pro
            420                 425                 430

Pro Lys Pro Lys Asp Thr Leu Met Ile Ala Arg Thr Pro Glu Val Thr
            435                 440                 445

Cys Val Val Val Asp Val Ser His Glu Asp Pro Glu Val Lys Phe Asn
            450                 455                 460

Trp Tyr Val Asp Gly Val Glu Val His Asn Ala Lys Thr Lys Pro Arg
465                 470                 475                 480

```
Glu Glu Gln Tyr Asn Ser Thr Tyr Arg Val Val Ser Val Leu Thr Val
                485                 490                 495

Leu His Gln Asp Trp Leu Asn Gly Lys Glu Tyr Lys Cys Lys Val Ser
            500                 505                 510

Asn Lys Ala Leu Pro Ala Pro Ile Glu Lys Thr Ile Ser Lys Ala Lys
        515                 520                 525

Pro Cys Pro Ala Pro Val Ala Gly Pro Ser Val Phe Leu Phe Pro
    530                 535                 540

Pro Lys Pro Lys Asp Thr Leu Met Ile Ala Arg Thr Pro Glu Val Thr
545                 550                 555                 560

Cys Val Val Val Asp Val Ser His Glu Asp Pro Glu Val Lys Phe Asn
                565                 570                 575

Trp Tyr Val Asp Gly Val Glu Val His Asn Ala Lys Thr Lys Pro Arg
                580                 585                 590

Glu Glu Gln Tyr Asn Ser Thr Tyr Arg Val Val Ser Val Leu Thr Val
                595                 600                 605

Leu His Gln Asp Trp Leu Asn Gly Lys Glu Tyr Lys Cys Lys Val Ser
            610                 615                 620

Asn Lys Ala Leu Pro Ala Pro Ile Glu Lys Thr Ile Ser Lys Ala Lys
625                 630                 635                 640

Met Ala Leu Ile Val Leu Gly Gly Val Ala Gly Leu Leu Leu Phe Ile
                645                 650                 655

Gly Leu Gly Ile Phe Phe Met Ala Leu Ile Val Leu Gly Gly Val Ala
                660                 665                 670

Gly Leu Leu Leu Phe Ile Gly Leu Gly Ile Phe Phe Cys Val Arg Cys
                675                 680                 685

Arg His Arg Arg Arg Ser Gly Gly Gly Ser Ser His Ile Gln Ile
            690                 695                 700

Pro Pro Gly Leu Thr Glu Leu Leu Gln Gly Tyr Thr Val Glu Val Leu
705                 710                 715                 720

Arg Gln Gln Pro Pro Asp Leu Val Glu Phe Ala Val Glu Tyr Phe Thr
                725                 730                 735

Arg Leu Arg Glu Ala Arg Ala
            740

<210> SEQ ID NO 37
<211> LENGTH: 719
<212> TYPE: PRT
<213> ORGANISM: Artificial Sequence
<220> FEATURE:
<223> OTHER INFORMATION: DDD1/AD1 ZipCAR control

<400> SEQUENCE: 37

Ala Asp Ala Pro Ala Tyr Gln Gln Gly Gln Asn Gln Leu Tyr Asn Glu
1               5                   10                  15

Leu Asn Leu Gly Arg Arg Glu Glu Tyr Asp Val Leu Asp Lys Arg Arg
                20                  25                  30

Gly Arg Asp Pro Glu Met Gly Gly Lys Pro Arg Arg Lys Asn Pro Gln
            35                  40                  45

Glu Gly Leu Tyr Asn Glu Leu Gln Lys Asp Lys Met Ala Glu Ala Tyr
        50                  55                  60

Ser Glu Ile Gly Met Lys Gly Glu Arg Arg Arg Gly Lys Gly His Asp
65                  70                  75                  80

Gly Leu Tyr Gln Gly Leu Ser Thr Ala Thr Lys Asp Thr Tyr Asp Ala
                85                  90                  95
```

```
Leu His Met Gln Ala Leu Pro Pro Arg Arg Ala Glu Gly Arg Gly Ser
            100                 105                 110

Leu Leu Thr Cys Gly Asp Val Glu Glu Asn Pro Gly Pro Met Ala Val
            115                 120                 125

Pro Thr Gln Val Leu Gly Leu Leu Leu Leu Trp Leu Thr Asp Ala Arg
        130                 135                 140

Cys Asp Ile Gln Met Thr Gln Ser Pro Ser Ser Leu Ser Ala Ser Val
145                 150                 155                 160

Gly Asp Arg Val Thr Ile Thr Cys Arg Ala Ser Glu Asp Ile Tyr Phe
                165                 170                 175

Asn Leu Val Trp Tyr Gln Gln Lys Pro Gly Lys Ala Pro Lys Leu Leu
            180                 185                 190

Ile Tyr Asp Thr Asn Arg Leu Ala Asp Gly Val Pro Ser Arg Phe Ser
        195                 200                 205

Gly Ser Gly Ser Gly Thr Gln Tyr Thr Leu Thr Ile Ser Ser Leu Gln
        210                 215                 220

Pro Glu Asp Phe Ala Thr Tyr Tyr Cys Gln His Tyr Lys Asn Tyr Pro
225                 230                 235                 240

Leu Thr Phe Gly Gln Gly Thr Lys Leu Glu Ile Lys Arg Ser Gly Gly
                245                 250                 255

Gly Gly Ser Gly Gly Gly Gly Ser Gly Gly Gly Ser Arg Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Phe Thr Leu Ser Asn Tyr Gly
        290                 295                 300

Met His Trp Ile Arg Gln Ala Pro Gly Lys Gly Leu Glu Trp Val Ser
305                 310                 315                 320

Ser Ile Ser Leu Asn Gly Gly Ser Thr Tyr Tyr Arg Asp Ser Val Lys
                325                 330                 335

Gly Arg Phe Thr Ile Ser Arg Asp Asn Ala Lys Ser Thr Leu Tyr Leu
            340                 345                 350

Gln Met Asn Ser Leu Arg Ala Glu Asp Thr Ala Val Tyr Tyr Cys Ala
        355                 360                 365

Ala Gln Asp Ala Tyr Thr Gly Gly Tyr Phe Asp Tyr Trp Gly Gln Gly
        370                 375                 380

Thr Leu Val Thr Val Ser Ser Met Pro Cys Pro Ala Pro Pro Val Ala
385                 390                 395                 400

Gly Pro Ser Val Phe Leu Phe Pro Pro Lys Pro Lys Asp Thr Leu Met
                405                 410                 415

Ile Ala Arg Thr Pro Glu Val Thr Cys Val Val Val Asp Val Ser His
            420                 425                 430

Glu Asp Pro Glu Val Lys Phe Asn Trp Tyr Val Asp Gly Val Glu Val
        435                 440                 445

His Asn Ala Lys Thr Lys Pro Arg Glu Glu Gln Tyr Asn Ser Thr Tyr
        450                 455                 460

Arg Val Val Ser Val Leu Thr Val Leu His Gln Asp Trp Leu Asn Gly
465                 470                 475                 480

Lys Glu Tyr Lys Cys Lys Val Ser Asn Lys Ala Leu Pro Ala Pro Ile
                485                 490                 495

Glu Lys Thr Ile Ser Lys Ala Lys Pro Cys Pro Ala Pro Pro Val Ala
            500                 505                 510

Gly Pro Ser Val Phe Leu Phe Pro Pro Lys Pro Lys Asp Thr Leu Met
```

```
                515                 520                 525
Ile Ala Arg Thr Pro Glu Val Thr Cys Val Val Val Asp Val Ser His
        530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
                580                 585                 590

Lys Glu Tyr Lys Cys Lys Val Ser Asn Lys Ala Leu Pro Ala Pro Ile
                595                 600                 605

Glu Lys Thr Ile Ser Lys Ala Lys Met Ala Leu Ile Val Leu Gly Gly
        610                 615                 620

Val Ala Gly Leu Leu Leu Phe Ile Gly Leu Gly Ile Phe Phe Met Ala
625                 630                 635                 640

Leu Ile Val Leu Gly Gly Val Ala Gly Leu Leu Leu Phe Ile Gly Leu
                645                 650                 655

Gly Ile Phe Phe Cys Val Arg Cys Arg His Arg Arg Arg Ser Gly Gly
                660                 665                 670

Gly Gly Ser Ser His Ile Gln Ile Pro Pro Gly Leu Thr Glu Leu Leu
        675                 680                 685

Gln Gly Tyr Thr Val Glu Val Leu Arg Gln Gln Pro Pro Asp Leu Val
        690                 695                 700

Glu Phe Ala Val Glu Tyr Phe Thr Arg Leu Arg Glu Ala Arg Ala
705                 710                 715
```

CHIMERIC ANTIGEN RECEPTOR SIGNALLING SYSTEM COMPRISING HETERODIMERIZATION DOMAINS

CROSS-REFERENCE TO RELATED APPLICATIONS

This application is the U.S. national stage of International (PCT) Application No. PCT/GB2016/050257, filed 4 Feb. 2016, incorporated herein by reference, which claims priority benefit of Application No. 1501936.7, filed on Feb. 5, 2015, in the United Kingdom.

INCORPORATION BY REFERENCE OF MATERIALS SUBMITTED ELECTRONICALLY

This application contains, as a separate part of the disclosure, a Sequence Listing in computer readable form (Filename: 52104_Seqlisting.txt; Size: 47,526 bytes; Created: Jul. 19, 2017), which is incorporated herein by reference in its entirety.

FIELD OF THE INVENTION

The present invention relates to an antigen receptor signalling system.

BACKGROUND TO THE INVENTION

Traditionally, antigen-specific T-cells have been generated by selective expansion of peripheral blood T-cells natively specific for the target antigen. However, it is difficult and quite often impossible to select and expand large numbers of T-cells specific for most cancer antigens. Gene-therapy with integrating vectors affords a solution to this problem as transgenic expression of Chimeric Antigen Receptor (CAR) allows generation of large numbers of T-cells specific to any surface antigen by ex vivo viral vector transduction of a bulk population of peripheral blood T-cells.

Chimeric antigen receptors are proteins which graft the specificity of an antigen binder, such as a monoclonal antibody (mAb), to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common forms of these molecules are fusions of single-chain variable fragments (scFv) derived from monoclonal antibodies which recognize a target antigen, fused via a spacer and a trans-membrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

A number of toxicities have been reported from CAR studies, and additional theoretical toxicities exist. Such toxicities include immunological toxicity caused by sustained intense activation of the CAR T-cells resulting in a macrophage activation syndrome (MAS) and "On-target off-tumour" toxicity i.e. recognition of the target antigen on normal tissues. MAS is presumed to be caused by persistent antigen-driven activation and proliferation of T-cells which in turn release copious inflammatory cytokines leading to hyper-activation of macrophages and a feed-forward cycle of immune activation. A large spike in serum IL-6 is characteristic and the syndrome can result in a severe systemic illness requiring ICU admission.

On-target off-tumour toxicity has been reported with other CARs, for example a group of patients treated with a CAR against the renal cell carcinoma antigen CAIX developed unexpected and treatment limiting biliary toxicity. Two fatalities have been reported with CAR studies: one patient died of a respiratory distress syndrome which occurred immediately post-infusion of a large dose of 3rd generation anti-ERBB2 CAR T-cells; a further patient died in a different study after a possible cytokine storm following treatment of CLL with a second generation anti-CD19 CAR.

These toxicities are very difficult to predict even with detailed animal studies or non-human primate work. Crucially, unlike small molecules and biologics, CAR T-cells do not have a half-life and one cannot cease administration and wait for the agent to breakdown/become excreted. CAR T-cells are autonomous and can engraft and proliferate. Toxicity can therefore be progressive and fulminant.

A key aspect of these toxicities is immune over-activation i.e. over-activation of CAR T-cells.

Suicide genes are genetically expressed elements which can conditionally destroy cells which express them. Examples include Herpes-simplex virus thymidine kinase, which renders cells susceptible to Ganciclovir; inducible Caspase 9, which renders cells susceptible to a small molecular homodimerizer and CD20 and RQR8, which renders cells susceptible to Rituximab.

This technology adds a certain amount of safety to CAR T-cell therapy, however there are limitations. Firstly, it is a binary approach wherein all the CAR T-cells are destroyed upon addition of the suicide entity. In addition, medicinal therapeutics often have a therapeutic window. With a suicide gene the potency of the product cannot be tuned such that efficacy with tolerable toxicity can be achieved. Secondly, it is not clear whether a suicide gene would help with some of the immune-toxicities described above: for instance by the time a macrophage activation syndrome had been triggered, it may well no longer need the CAR T-cells to perpetuate and the suicide gene would no longer be helpful. The more acute cytokine release syndromes probably occur too quickly for the suicide gene to work. Finally, suicide genes are not "fail-safe", i.e. the default status is for the CAR T-cells to be active.

There is thus a need for alternative methods for controlling CAR T-cells that are not associated with the disadvantages and problems mentioned above.

SUMMARY OF ASPECTS OF THE INVENTION

The present inventors have found that it is possible to separate the antigen-recognition and signalling components of a CAR to produce a system in which signalling only occurs when the antigen-recognition and signalling components dimerize and form a functional CAR complex.

Thus in a first aspect the present invention relates to a chimeric antigen-receptor (CAR) signalling system comprising;

(i) a targeting component comprising an antigen-binding domain, a transmembrane domain and a first heterodimerization domain; and (ii) an intracellular signalling component comprising a signalling domain and a second heterodimerization domain;

wherein spontaneous heterodimerization between the first and second heterodimerization domains causes the targeting component and signalling component to form a functional CAR complex.

The first and second heterodimerization domains are capable of spontaneous dimerization with each other. Heterodimerization occurs with the first and second heterodimerization domains alone, without the need for any separate molecule acting as an "inducer" of dimerization.

The first and second heterodimerization domains may comprise leucine zipper domains, DDD1 and AD1 domains, Barnase and Barstar domains or human pancreatic RNAse and S-peptide domains.

The CAR signalling system may comprise multiple targeting components, each recognizing a different antigen.

The first heterodimerization domains of the multiple targeting components may differ in affinity for the second heterodimerization domain such that each antigen propagates different signalling strengths.

The signalling domain of the signalling component may comprise a single endodomain selected from CD3 zeta endodomain, CD28 endodomain, 41BB endodomain, OX40 endodomain, an ICOS endodomain, a CD27 endodomain, a BTLA endodomain, a CD30 endodomain, a GITR endodomain and an HVEM endodomain.

The signalling domain of the signalling component may comprise at least one of CD3 zeta endodomain, CD28 endodomain, 41BB endodomain and OX40 endodomain.

The CAR signalling system may comprise a plurality of signalling components, each comprising a signalling domain and a second heterodimerization domain, wherein the second heterodimerization domains each recognise the same first heterodimerization domain but the signalling domains comprise different signalling endodomains.

The CAR signalling system may comprise a plurality of signalling components which comprise a plurality of second heterodimerization domains, each of which independently recognise the first heterodimerization domains with different affinities.

In the CAR signalling system of the first aspect of the invention, the targeting component may comprise more than two heterodimerisation domains, such that a single targeting component is capable of heterodimerising with more than two signalling components. For example, the targeting component may comprise from 3 to 12 heterodimerisation domains. The targeting component may comprise 4, 6, 8 or 10 heterodimerization domains.

Each signalling component may comprise a plurality of signalling domains, which may be the same or different. For example, each signalling component may comprise two, three or four copies of the same signalling domain, such as CD3 zeta.

In a second aspect, the present invention provides a targeting component suitable for use in the CAR signalling system according to the first aspect of the invention which comprises an antigen-binding domain, a transmembrane domain and a heterodimerization domain.

The targeting component may comprise a plurality of heterodimerization domains, such as more than two heterodimerisation domains.

In a third aspect, the present invention comprises a signalling component suitable for use in the CAR signalling system according to the first aspect of the invention which comprises a signalling domain and a heterodimerization domain.

The signalling component may comprise a plurality of signalling domains.

In a fourth aspect, the present invention provides a nucleic acid encoding the targeting component according to the second aspect of the invention.

In a fifth aspect, the present invention provides a nucleic acid encoding the signalling component according the third aspect of the invention.

In a sixth aspect, the present invention provides a nucleic acid construct encoding a CAR signalling system according the first aspect of the invention, wherein the nucleic acid construct comprises the following structure:

A-X—B in which

A and B are nucleic acid sequences encoding a targeting component or a signalling component as defined in the second or third aspect of the present invention; and X is a nucleic acid sequence which encodes a cleavage site, such that A is cleaved from B after translation.

The nucleic acid construct may have one of the following structures:

a) AbD-spacer-TM-endo-Het1-coexpr-Het2-SD b) AbD-spacer-TM-endo-Het1-coexpr-SD-Het2 c) Het2-SD-coexpr-AbD-spacer-TM-endo-Het1 or d) SD-Het2-coexpr-AbD-spacer-TM-endo-Het1 in which

AbD is a nucleic acid sequence encoding the antigen-binding domain of the targeting molecule;

spacer is a nucleic acid sequence encoding a spacer of the targeting molecule;

TM is a nucleic acid sequence encoding the transmembrane domain of the targeting molecule;

endo is a nucleic acid sequence encoding the endodomain of the targeting molecule;

Het1 is a nucleic acid sequence encoding the heterodimerization motif of the targeting molecule;

coexpr is a nucleic acid sequence encoding a cleavage site;

Het2 is a nucleic acid sequence encoding the heterodimerization motif of the signalling molecule; and SD is nucleic acid sequence encoding the signalling domain of the signalling molecule.

The nucleic acid construct may encode multiple targeting components and/or multiple signalling components as defined in the first aspect of the present invention, wherein the multiple targeting components or multiple signalling components are separated by cleavage sites, such that the multiple targeting components or multiple signalling components are cleaved after translation.

In a seventh aspect, the present invention provides a vector comprising a nucleic acid according to the fourth or fifth aspect of the invention or a nucleic acid construct according to the sixth aspect of the present invention.

The vector may be a retroviral vector or a lentiviral vector or a transposon.

In an eighth aspect, the present invention provides a cell which comprises a CAR signalling system according to the first aspect of the present invention.

In a ninth aspect, the present invention provides a cell which expresses at least one targeting component according to the second aspect of the invention and at least one signalling component according to the third aspect of the invention.

The cell may comprise a nucleic acid according to fourth or fifth aspect of the invention or a nucleic acid construct according to the sixth aspect of the present invention or a vector according to the seventh aspect of the present invention.

The cell may be a T cell or NK cell.

In tenth aspect, the present invention provides a pharmaceutical composition comprising a plurality of cells according to the ninth aspect of the invention.

In an eleventh aspect, the present invention provides a pharmaceutical composition according to the tenth aspect of the invention for use in treating and/or preventing a disease.

In a twelfth aspect, the present invention relates to a method for treating and/or preventing a disease, which comprises the step of administering a pharmaceutical composition according to the tenth aspect of the invention to a subject.

The method may comprise the following steps:
(i) isolation of a T cell or NK cell containing sample from a subject;
(ii) transduction or transfection of the T cells or NK cells with a nucleic acid according to the fourth or fifth aspect of the invention or a nucleic acid construct according to the to sixth aspect of the present invention or a vector according to the seventh aspects of the present invention; and
(iii) administering the T cells or NK cells from (ii) to the subject.

In a thirteenth aspect, the present invention relates to the use of a pharmaceutical composition according to the tenth aspect of the present invention in the manufacture of a medicament for the treatment and/or prevention of a disease.

The disease may be cancer.

In a fourteenth aspect, the present invention provides a kit which comprises a nucleic acid according to the fourth or fifth aspect of the invention or a nucleic acid construct according to the sixth aspect of the present invention or a vector according to the seventh aspect of the present invention.

The kit may comprise a cell according to the ninth aspect of the present invention.

In a sixteenth aspect, the present invention provides a method for making a cell according to the ninth aspect of the invention, which comprises the step of introducing a nucleic acid according to the fourth or fifth aspect of the invention or a nucleic acid construct according to any of the sixth aspect of the present invention or a vector according to the seventh aspects of the present invention, into the cell.

The cell may be from a sample isolated from a subject.

The CAR signalling system of the present invention provides several advantages compared to classic CAR molecules. For example, steric hindrance of second messengers can be avoided because the signalling domains may be independent of each other (i.e. provided on separate signalling components).

Further, it is possible to include a plurality of different signalling molecules and different signalling domain(s) may be provided on separate signalling components. As such each signalling domain may be proximal to the membrane. This proximity to the membrane is optimal for signalling. This is in contrast to a classic CAR, in which the signalling domain becomes crowded and the most distal element may be too far from the membrane.

It is possible to amplify the T-cell activation signal by recruiting multiple signalling components for each antigen recognition molecule. This is especially useful for the detection of low density antigens.

In addition, by altering the affinity of the heterodimerization domain on the signalling component, it is possible to "tune" the mix of co-stimulatory signals the T-cell receives. For instance, it might be advantageous for the T-cell to receive a high level of OX40 signal, intermediate amounts of Zeta signal and low amounts of CD28. Such a signal may lead, for example, to a slow but steady rejection of a tumour and thus avoid immune-toxicity and encourage T-cell persistence.

It is also possible to target multiple antigens more conveniently since the signalling components are shared. In this case, two targeting components may be co-expressed along with the signalling components. In the case of targeting more than one antigen, if one antigen is more densely expressed than another, the heterodimerization domains on the respective targeting domains can be altered such that the signalling components interact with each targeting component in order to create a balanced signal for recognition of each antigen. In this way, a very versatile and tunable CAR signalling system can be constructed.

DESCRIPTION OF THE FIGURES

FIG. 11—Amino acid sequences of the constructs depicted in FIG. 4.

DETAILED DESCRIPTION OF THE INVENTION

Chimeric Antigen Receptors (CARs)

Figure 1:
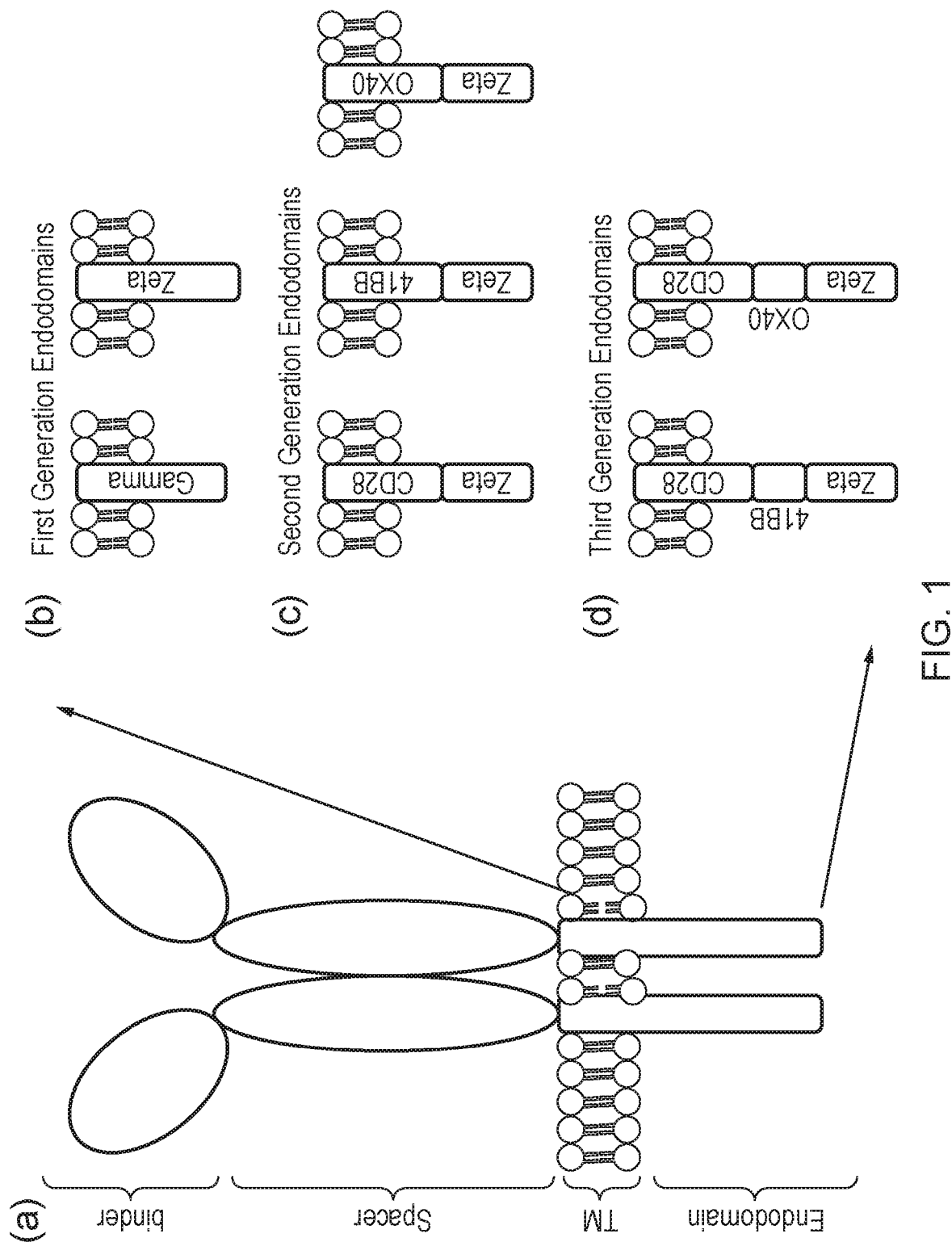
FIG. 1—a) Schematic diagram illustrating a classical CAR. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in the same compound endodomain.
Figure 2:
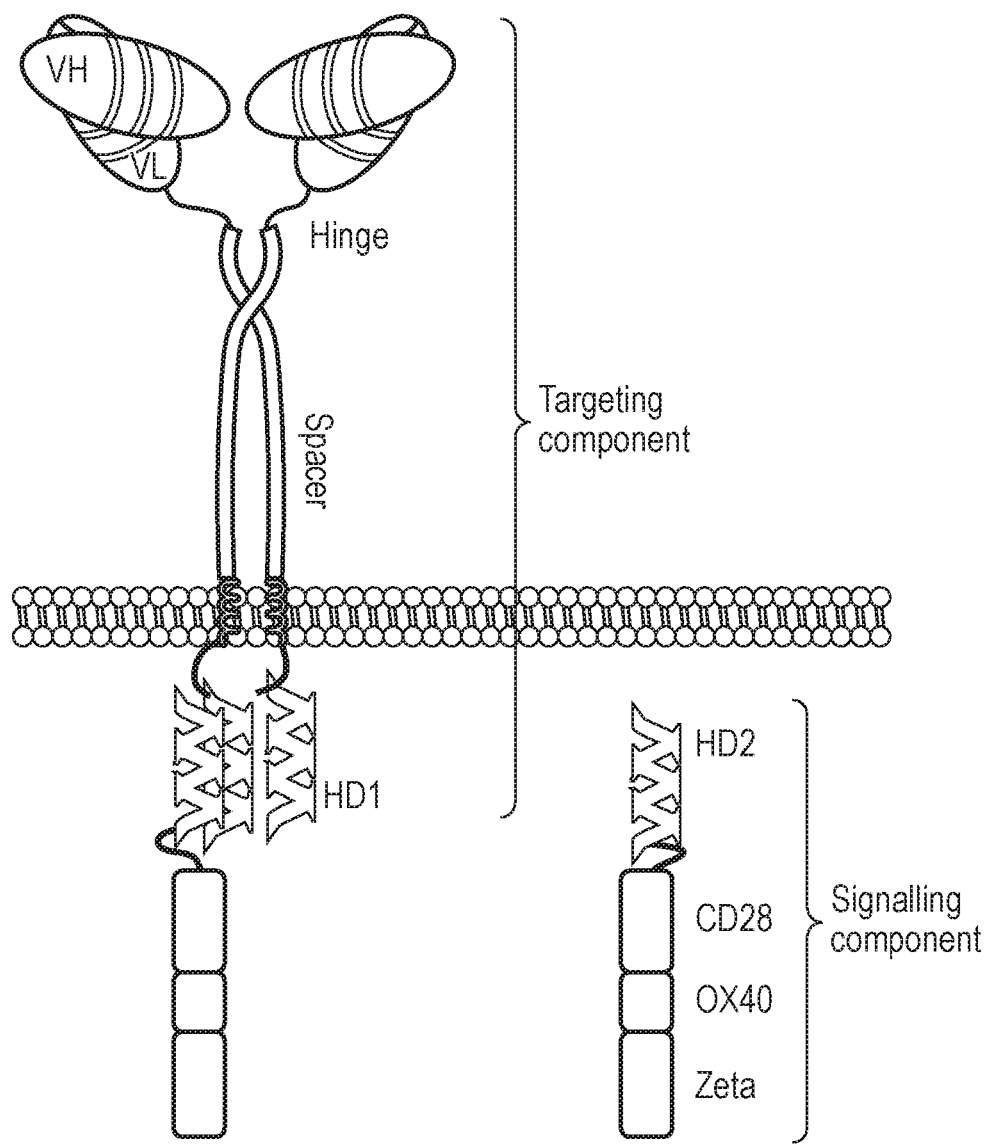
FIG. 2—Concept of a zipCAR. The targeting component is a type I transmembrane protein whose ectodomain comprises a target recognition domain and a spacer, and whose endodomain comprises a heterodimerization motif (HD1). The signalling component is an intracellular protein and comprises a heterodimerization motif (HD2) fused to a signalling domain. While the two components are separate proteins, they assemble after expression to form a functional CAR.

Classical CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like or ligand-based antigen binding site. A spacer domain may be necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

In a first aspect, the present invention relates to a CAR system in which the antigen-recognizing/antigen binding domain and transmembrane domain are provided on a first molecule (termed herein 'targeting component'), which localizes to the cell membrane. The intracellular signalling domain is provided on a second, intracellular molecule (termed herein 'signalling component').

Importantly, the targeting component comprises a first heterodimerization domain and the signalling component comprises a second heterodimerization domain. The first and second heterodimerization domains are capable of dimerization with one another. Binding of the first and second heterodimerization domains causes co-localization of the targeting component and the signalling component at the cell surface. This forms a functional CAR complex at the cell surface and thus, when antigen binds to the antigen binding domain of the targeting component, there is signalling through the signalling component.

Herein 'co-localization' or 'heterodimerization' of the targeting and signalling components is analogous to ligation/recruitment of the signalling component to the targeting component via binding of the first heterodimerization domain of the targeting component and the second heterodimerization domain of the signalling component.

Signalling through the signalling component may be determined by a variety of methods known in the art. Such methods include assaying signal transduction, for example assaying levels of specific protein tyrosine kinases (PTKs), breakdown of phosphatidylinositol 4,5-biphosphate (PIP2), activation of protein kinase C (PKC) and elevation of intracellular calcium ion concentration. Functional readouts, such as clonal expansion of T cells, upregulation of activation markers on the cell surface, differentiation into effector cells and induction of cytotoxicity or cytokine secretion may also be utilised. As an illustration, in the present examples the inventors determined levels of interleukin-2 (IL-2) produced by T-cells expressing a targeting component and signalling component of the CAR system according to the present invention upon binding of antigen to the receptor component in the presence of varying concentrations of an agent.

First and Second Heterodimerization Domains

The first and second heterodimerization domains of the present CAR system may be any combination of domains which interact resulting in co-localization of the targeting component and signalling component at the cell membrane.

As such, the first heterodimerization domain and second heterodimerization domain may be capable of specifically binding to one another.

The first and second heterodimerization domains are capable of spontaneous dimerization with each other. Heterodimerization occurs with the first and second heterodimerization domains alone, without the need for any separate molecule acting as an "inducer" of dimerization.

The signalling system of the present invention is not limited by the arrangement of a specific pair of heterodimerization domains. The targeting component may comprise either domain from a pair of heterodimerizing domains so long as the signalling component comprises the corresponding, complementary domain which enables the targeting component and the signalling component to co-localize at the cell membrane.

The heterodimerization domains for use in the present CAR system are not limited to those which interact at a 1:1 ratio. For example, heterodimerization domains may interact to form multimers (e.g. trimers or tetramers). The domains may interact in a manner which co-localises a single first heterodimerization domain with multiple (e.g. 2 or 3) second heterodimerization domains. Herein it may be advantageous to have a signalling domain which comprises the second heterodimerization domain, such that multiple signalling components can co-localise with a single targeting component. This may be advantageous, for example, when a high level of signalling is required upon binding of antigen to the targeting component.

Figure 12:
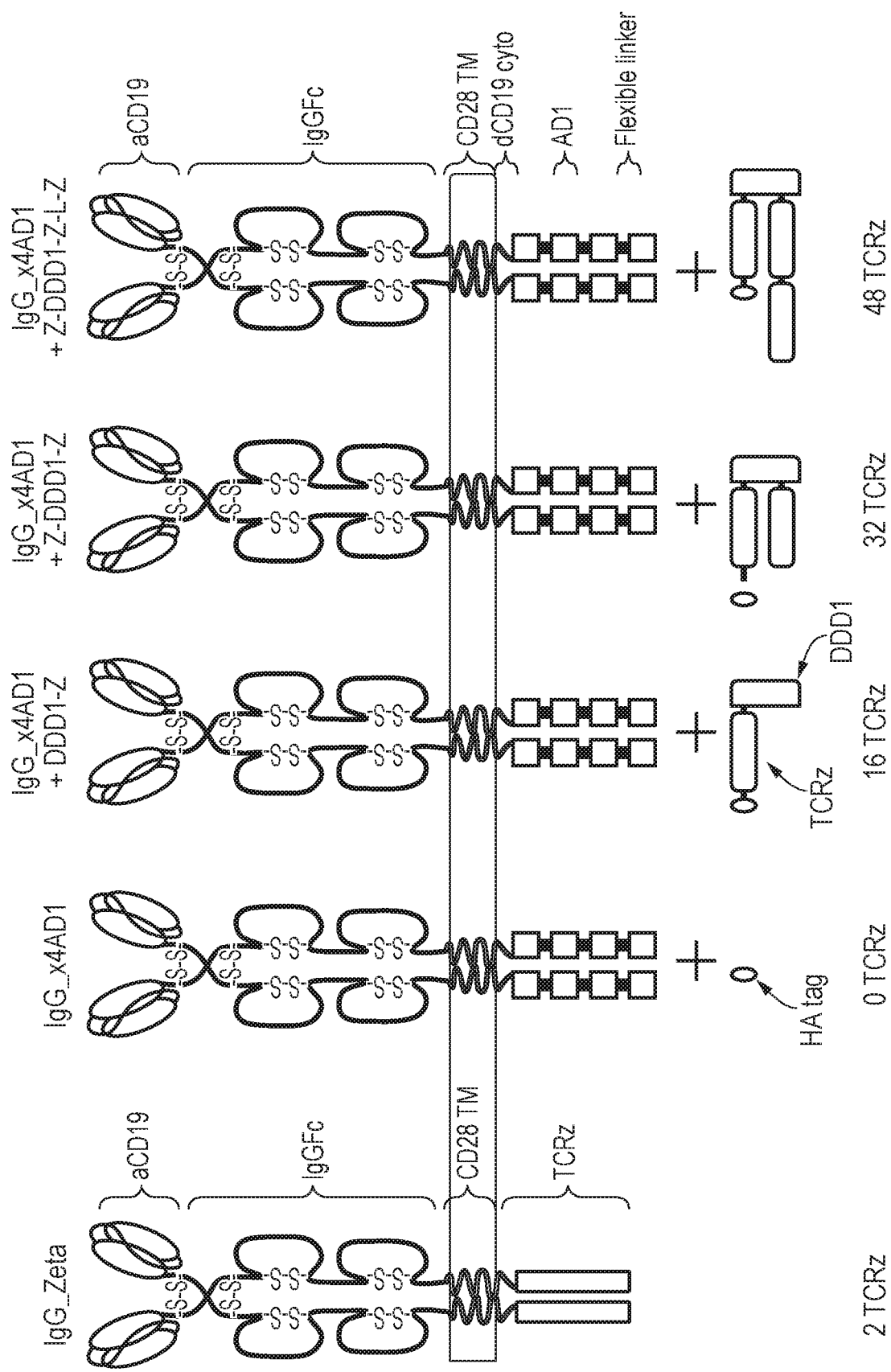
FIG. 12—Schematic illustration of a "superCAR" ZipCAR with multiple heterodimerisation domains. An anti-CD19 targeting component was engineered to express eight heterodimerisation domains. The effect on-cell activation was tested with various signalling components: HA tag alone (control); HA tag, heterodimerisation domain and one TCRzeta; HA tag, heterodimerisation domain and two TCRzeta domains; HA tag, heterodimerisation domain and three TCRzeta domains.

The targeting component may comprise a plurality of heterodimerization domains, so that it interacts with a plurality of signalling components. For example, the targeting component may comprise more than two heterodimerization domains, such a 3 to 10 heterodimerization domains. FIG. 12 shows a targeting component which comprises 8 heterodimerization domains.

For convenience, the term heterodimerization domain is used herein for all domains which mediate co-localization the targeting and signalling components.

A large variety of appropriate heterodimerization domains are known in the art, examples of which are provided herein.

The first and second heterodimerization domains may be leucine zippers.

Leucine zippers are well known in the art (see Hakoshima; *Encyclopedia of Life Sciences;* 2005, for example). The leucine zipper is a super-secondary structure that functions as a dimerization domain. Its presence generates adhesion forces in parallel alpha helices. A single leucine zipper consists of multiple leucine residues at approximately 7-residue intervals, which forms an amphipathic alpha helix with a hydrophobic region running along one side. This hydrophobic region provides an area for dimerization, allowing the motifs to "zip" together. Leucine zippers are typically 20 to 40 amino acids in length, for example approximately 30 amino acids.

The first and/or second heterodimerization domain may comprise the sequence shown as SEQ ID NO: 1 or 2. The first heterodimerization domain may comprise the sequence shown as SEQ ID NO: 1 and the second heterodimerization domain may comprise the sequence shown as SEQ ID NO: 2, or vice versa.

SEQ ID NO: 1:   QLEKELQALEKENAQLEWELQALEKELAQ

SEQ ID NO: 2:   QLEKKLQALKKKNAQLKWKLQALKKKLAQ

In certain embodiments, the first and second heterodimerization domains may be acidic (e.g. SEQ ID NO: 1) or basic (e.g. SEQ ID NO: 2) leucine zippers. In particular, where the first heterodimerization domain is an acidic leucine zipper, the second heterodimerization is a basic leucine zipper and vice versa.

The first and second heterodimerization domains may be dimerization and docking domain (DDD1) and anchoring domain (AD1). These domains and the interaction between them is known in the art (Rossi et al.; PNAS; 2006; 103(18); 6841-6846).

DDD1 is a short alpha helical structure derived from Protein Kinase A (PKA). AD1 is a short alpha helical structure derived from A-kinase anchor proteins (AKAPs).

The DDD1 domain may comprise the sequence shown as SEQ ID NO: 3.

SEQ ID NO: 3:
SHIQIPPGLTELLQGYTVEVLRQQPPDLVEFAVEYFTRLREARA

The AD1 domain may comprise the sequence shown as SEQ ID NO: 4

SEQ ID NO: 4:   VQIEYLAKQIVDNAIQQA

Since the DDD1/AD1 interaction is trimeric, an AD1 domain present on the targeting component will recruit four signalling domains comprising a DDD1 domain. Thus in a particular embodiment, the targeting component comprises an AD1 domain and the receptor component comprises a DDD1 domain.

The heterodimerization domains may be derived from the Bacterial Ribonuclease (Barnase) and Barstar peptides.

Barnase is the *Bacillus amyloliquefaciens* ribonuclease protein. It is composed on 110 amino acids. Barstar functions to inhibit the nuclease activity of Barnase and therefore binds Barstar with a very high affinity (an on-rate of $10^8$ $s^{-1}M^{-1}$).

The heterodimerization domains may be derived from Human Pancreatic RNases and S-peptide.

Human Pancreatic RNase are pyrimidine-specific endonucleases. S-peptide is the enzymatically inactive proteolytic fragment of RNase A, which lacks the RNA binding site.

The present invention also encompasses variants of the heterodimerization sequences described herein which retain the ability to dimerize with the corresponding heterodimerization domain. The heterodimerization domain may be a variant having 5, 4, 3, 2 or 1 amino acid mutations (insertions, substitutions or additions) provided that domain still functions to cause co-localization of the targeting component and signalling component at the cell membrane.

A variant sequence may have at least 80%, 85%, 90%, 95%, 98% or 99% sequence identity to a sequence of a heterodimerization domain described herein, provided that the sequence still functions to cause co-localization of the targeting component and signalling component at the cell membrane.

Targeting Component

The term targeting component is analogous to 'receptor component'.

The present invention provides a targeting component comprising an antigen-binding domain, an optional spacer domain, a transmembrane domain and a first heterodimerization domain. When expressed in a cell, the targeting component localises to the cell membrane. Here, the antigen-binding domain of the molecule is orientated on the extracellular side of the membrane and the first heterodimerization domain is localised to the intracellular side of the membrane.

The targeting component therefore provides the antigen-binding function of the CAR system of the present invention.

Antigen Binding Domain

The antigen-binding domain is the portion of a classical CAR which recognizes antigen. In the signalling system of the present invention the antigen-binding is located within the targeting component.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

Various tumour associated antigens (TAA) are known, as shown in the following Table 1. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Transmemebrane Domain

The transmembrane domain is the sequence of a classical CAR that spans the membrane. In the signalling system of the present invention the transmembrane domain is located in the targeting component. It may comprise a hydrophobic alpha helix. The transmembrane domain may be derived from CD28, which gives good receptor stability.

Signal Peptide

The targeting component of the CAR system of the present invention may comprise a signal peptide so that when the targeting component is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the sequence shown as SEQ ID NO: 5, 6 or 7 or a variant thereof having 5, 4, 3, 2 or 1 amino acid mutations (insertions, substitutions or additions) provided that the signal peptide still functions to cause cell surface expression of the CAR.

SEQ ID NO: 5: MGTSLLCWMALCLLGADHADG

The signal peptide of SEQ ID NO: 5 is compact and highly efficient. It is predicted to give about 95% cleavage after the terminal glycine, giving efficient removal by signal peptidase.

SEQ ID NO: 6: MSLPVTALLLPLALLLHAARP

The signal peptide of SEQ ID NO: 6 is derived from IgG1.

SEQ ID NO: 7: MAVPTQVLGLLLLWLTDARC

The signal peptide of SEQ ID NO: 7 is derived from CD8.

Spacer Domain

The CAR system described herein may comprise a spacer sequence to connect the antigen-binding domain with the transmembrane domain in the targeting component. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

```
SEQ ID NO: 8 (hinge-CH2CH3 of human IgG1)
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD

SEQ ID NO: 9 (human CD8 stalk):
TTTPAPRPPTPAPTIASQPLSLRPEACRPAAGGAVHTRGLDFACDI

SEQ ID NO: 10 (human IgG1 hinge):
AEPKSPDKTHTCPPCPKDPK
```

-continued

SEQ ID NO: 11 (CD2 ectodomain)
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCPEKGLD

SEQ ID NO: 12 (CD34 ectodomain)
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT

Targeting Component Comprising a Plurality of First Heterodimerization Domains The targeting component may comprise a plurality of first heterodimerization domains and thus be capable of recruiting more than one signalling component.

The plurality of first heterodimerization domains may be present in a single intracellular domain of the receptor component.

The targeting component may comprise an appropriate number of transmembrane domains such that each first binding domain is orientated on the intracellular side of the cell membrane. For example the targeting component may comprise 3, 5, 7, 9, 11, or more transmembrane domains. In this way, a single targeting component may recruit multiple signalling components amplifying signalling in response to antigen.

The first heterodimerization domains may each be variants which have a different affinity for the second heterodimerization domain of the signalling component.

Multiple Targeting Components

Figure 9:
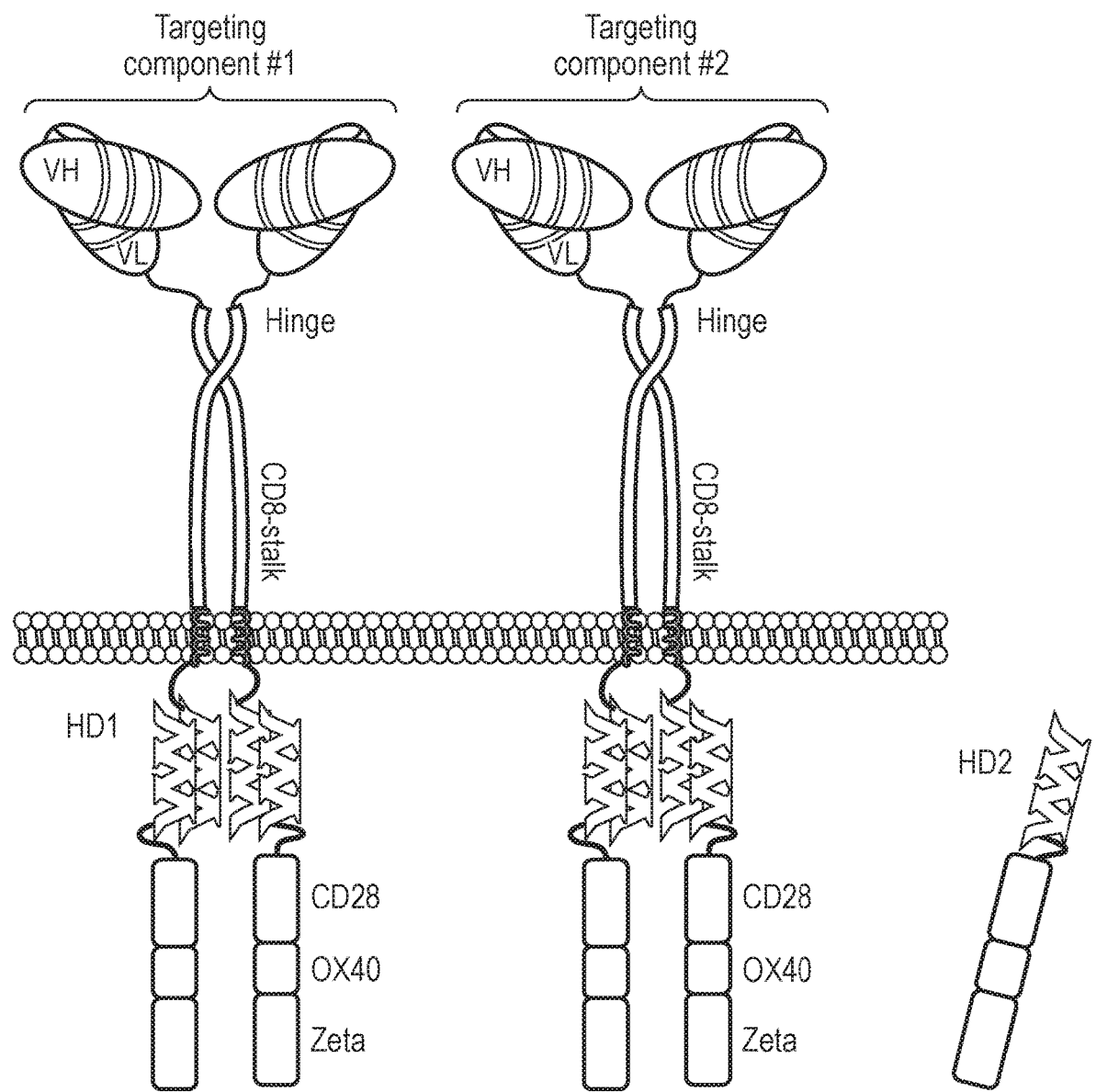
FIG. 9—ZipCAR with multiple targeting components. Multiple different targeting components are expressed and each targeting component recognizes a different antigen. The signalling components are capable of interacting with each targeting component and hence a cell expressing such a CAR signalling system is capable of recognizing each of the antigens recognized by the targeting components.
Figure 10:
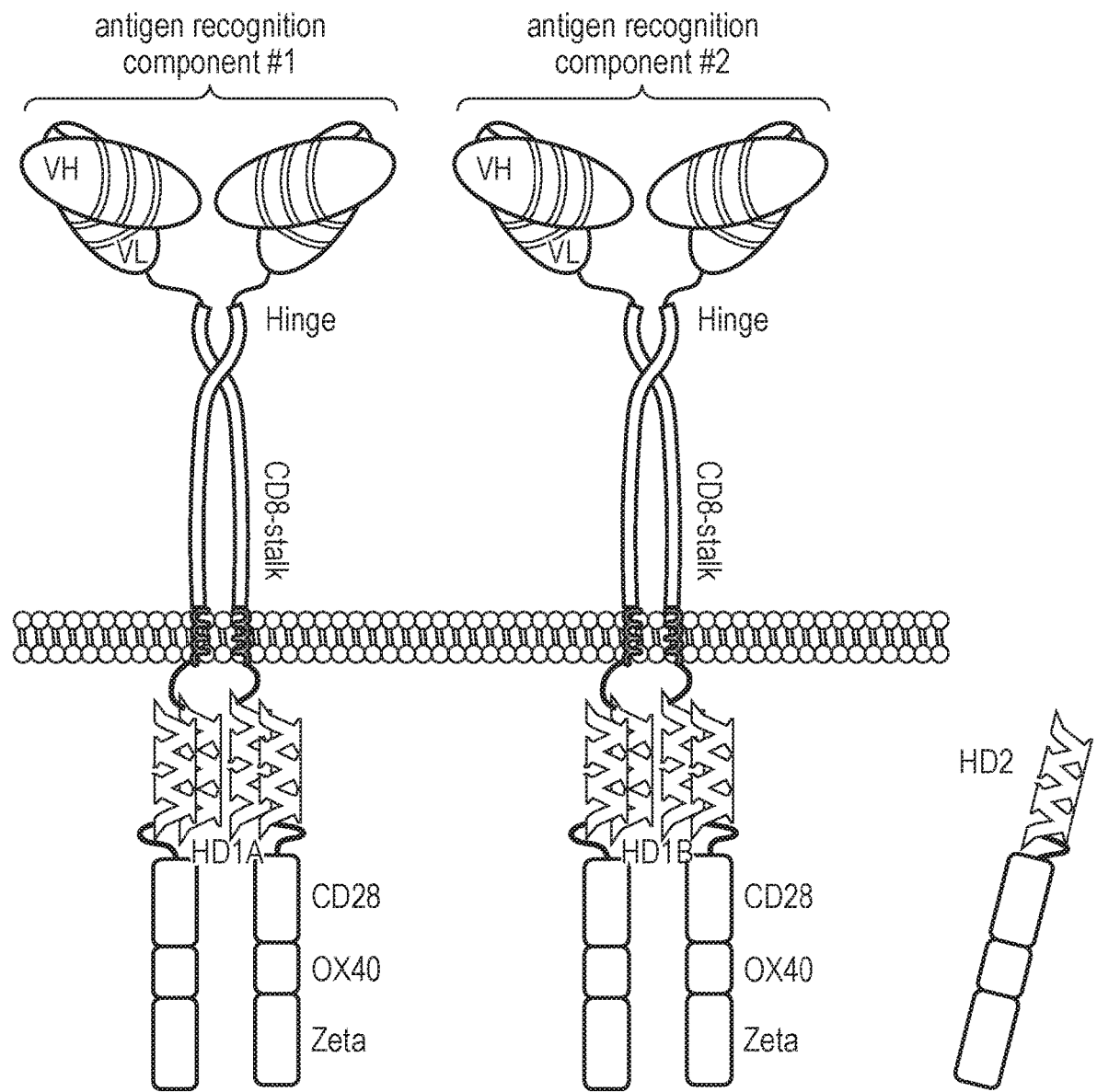
FIG. 10—ZipCAR with multiple targeting components with different heterodimerization domains. Multiple different targeting components are expressed and each targeting component recognizes a different antigen. The heterodimerization domain of each targeting component (HD1) differs such that each targeting component recruits signalling components with different kinetics. Consequently, binding of different cognate antigens results in different signalling intensities.

In another embodiment of the invention, the CAR system may comprise two or more targeting components each recognizing different antigens but comprising of the same intracellular heterodimerization domain. Such a CAR system would be capable of recognizing multiple antigens (FIGS. 9 and 10). This might be useful for instance in avoiding tumour escape.

In a further related aspect of the invention, the first heterodimerization domains of the targeting components differ in residues which dictate their affinity for the second heterodimerization domain of the signalling component. In this way, a CAR system can be tuned such that signalling in response to one antigen is greater or less than the response to another (FIG. 10). This might be useful for instance when targeting two tumour antigens simultaneously but one is expressed at a higher density than the other. Response to this antigen could be tuned down to avoid toxicity caused by over-stimulation.

Methods suitable for altering the amino acid residues of the first or second heterodimerization domain such that the binding affinity between the two domains is altered are known in the art and include substitution, addition and removal of amino acids using both targeted and random mutagenesis. Methods for determining the binding affinity between a first heterodimerization domain and a second heterodimerization domain are also well known in the art and include bioinformatics prediction of protein-protein interactions, affinity electrophoresis, surface plasma resonance, bio-layer interferometry, dual polarisation interferometry, static light scattering and dynamic light scattering.

Intracellular Signalling Component

The present invention also provides a signalling component comprising a signalling domain and a second heterodimerization domain. The signalling component is a soluble molecule and thus localises to the cytoplasm when it is expressed in a cell, for example a T cell.

No signalling occurs through the signalling domain of the signalling component unless it is co-localised with the targeting component provided by the present invention.

Intracellular Signalling Domain

The intracellular signalling domain is the signal-transmission portion of a classical CAR. In the signalling system of the present invention, the intracellular signalling domain (signalling domain) is part of the signalling component. When expressed in a cell, for example a T cell, the membrane-bound, targeting component and the intracellular signalling component are brought into proximity via the interaction between the first and second heterodimerization domains. After antigen recognition, receptors cluster, native CD45 and CD148 are excluded from the synapse and a signal is transmitted to the cell.

As such, the signalling domain of the signalling component is analogous to the endodomain of a classical CAR molecule.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 1B).

The signalling component described herein comprises a signalling domain; it may comprise the CD3-Zeta endodomain alone, the CD3-Zeta endodomain with that of either CD28 or OX40 or the CD28 endodomain and OX40 and CD3-Zeta endodomain (FIG. 1).

The signalling component may comprise one or more of the following: an ICOS endodomain, a CD27 endodomain, a BTLA endodomain, a CD30 endodomain, a GITR endodomain and an HVEM endodomain.

The signalling component of a CAR system according to the present invention may comprise the sequence shown as SEQ ID NO: 13 to 21 or a variant thereof having at least 80% sequence identity.

CD3 Z endodomain
SEQ ID NO: 13
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD28 and CD3 Zeta endodomains
SEQ ID NO: 14
SKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

-continued

CD28, OX40 and CD3 Zeta endodomains
SEQ ID NO: 15
SKRSRLLHSDYMNMTPRRPGPTRKHYQPYAPPRDFAAYRSRDQRLPPDAH

KPPGGGSFRTPIQEEQADAHSTLAKIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

ICOS endodomain
SEQ ID No. 16
CWLTKKKYSSSVHDPNGEYMFMRAVNTAKKSRLTDVTL

CD27 endodomain
SEQ ID No. 17
QRRKYRSNKGESPVEPAEPCHYSCPREEEGSTIPIQEDYRKPEPACSP

BTLA endodomain
SEQ ID No. 18
RRHQGKQNELSDTAGREINLVDAHLKSEQTEASTRQNSQVLLSETGIYDN

DPDLCFRMQEGSEVYSNPCLEENKPGIVYASLNHSVIGPNSRLARNVKEA

PTEYASICVRS

CD30 endodomain
SEQ ID No. 19
HRRACRKRIRQKLHLCYPVQTSQPKLELVDSRPRRSSTQLRSGASVTEPV

AEERGLMSQPLMETCHSVGAAYLESLPLQDASPAGGPSSPRDLPEPRVST

EHTNNKIEKIYIMKADTVIVGTVKAELPEGRGLAGPAEPELEEELEADHT

PHYPEQETEPPLGSCSDVMLSVEEEGKEDPLPTAASGK

GITR endodomain
SEQ ID No. 20
QLGLHIWQLRSQCMWPRETQLLLEVPPSTEDARSCQFPEEERGERSAEEK

GRLGDLWV

HVEM endodomain
SEQ ID No. 21
CVKRRKPRGDVVKVIVSVQRKRQEAEGEATVIEALQAPPDVTTVAVEETI

PSFTGRSPNH

A variant sequence may have at least 80%, 85%, 90%, 95%, 98% or 99% sequence identity to SEQ ID NO: 13 to 21 provided that the sequence provides an effective intracellular signalling domain.

The intracellular signalling component may comprise a plurality of signalling domains, for example, 2 to 5 signalling domains, which may be the same or different. In particular the signalling component may comprise 2 or 3 copies of the same intracellular signalling domain.

Multiple Signalling Components

Figure 7:
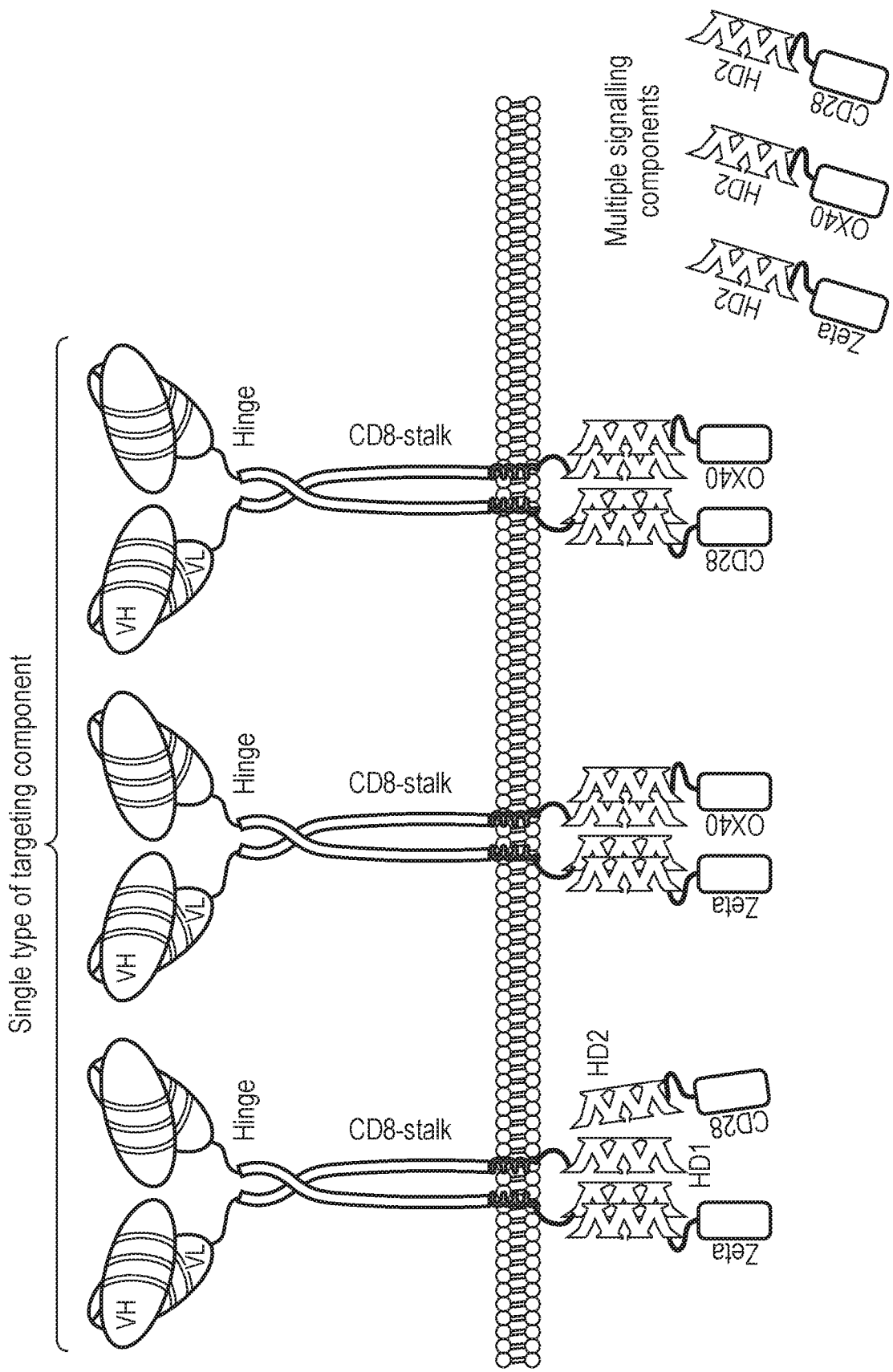
FIG. 7—zipCAR with multiple signalling components. The multiple signalling components interact with the targeting component(s) such that a multitude of signals can be transmitted.
Figure 8:
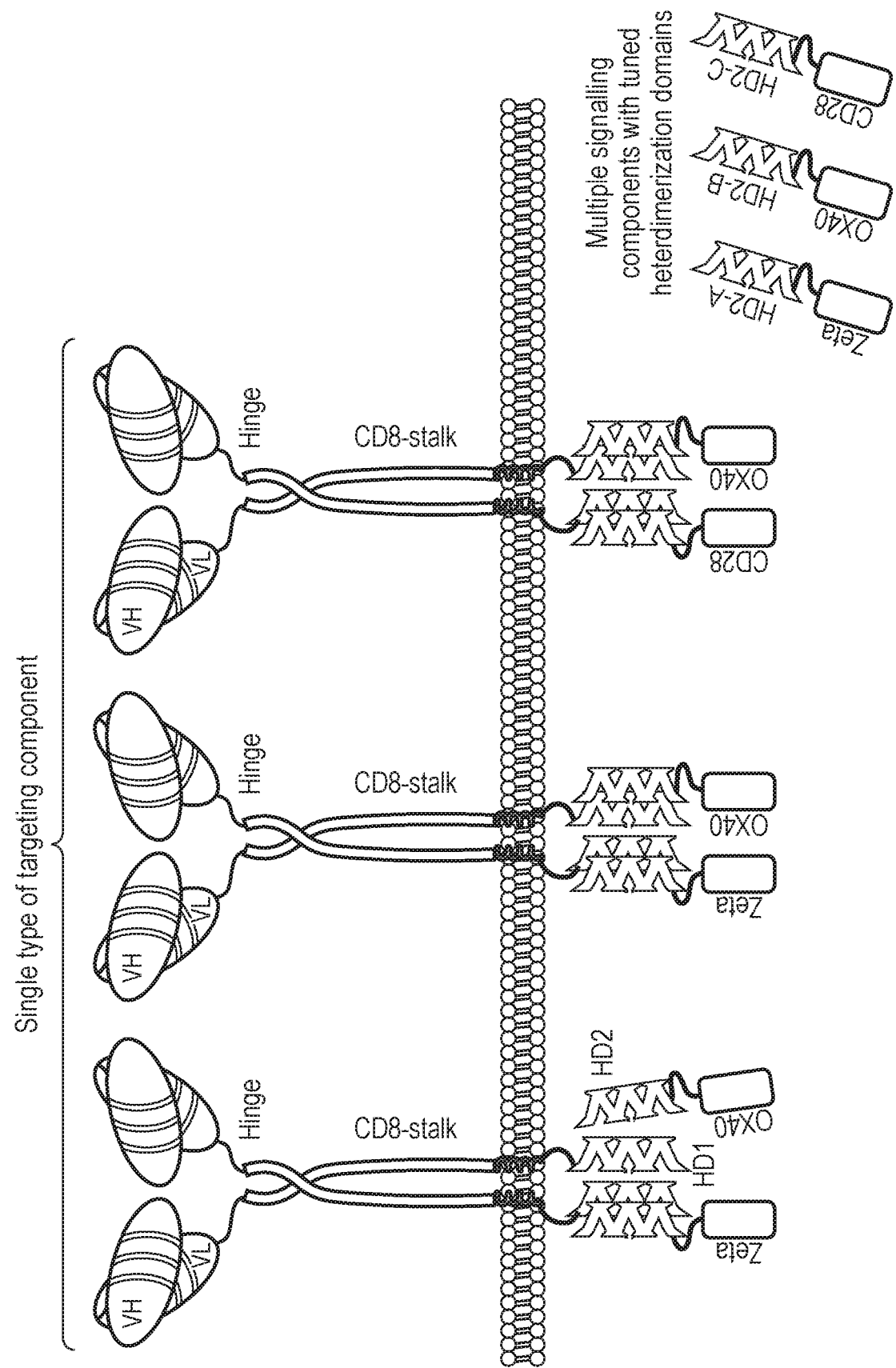
FIG. 8—ZipCAR with multiple signalling components with altered heterodimerization motifs. Multiple signalling components are expressed which interact with the targeting component(s). The heterodimerization domains of the different signalling components (HD2) are have differing affinities for the heterodimerization domains of the targeting components (HD1). In this way a multitude of signals can be transmitted in trans where the average intensity of each signal can be tuned.

The signalling system according to the first aspect of the present invention may comprise a plurality of signalling components, each comprising a signalling domain and a second heterodimerization domain, wherein each second binding domain is bound by the same first binding domain of the receptor component but the signalling domains comprise different endodomains (FIGS. 7 and 8). In this way, multiple different endodomains can be activated simultaneously. This is advantageous over a compound signalling domain since each signalling domain remains unencumbered from other signalling domains.

If each signalling component comprises a second heterodimerization domain which differs in residues which alter their affinity to the first heterodimerization domain of the receptor component, the signalling components comprising different signalling domains will ligate to the first binding domain with differing kinetics (FIG. 8). This allows greater control over the signalling in response to antigen-binding by the receptor component as different signalling components are recruited to the receptor component in varying kinetics/dynamics. This is advantageous since rather than a fixed equal ratio of signal transmitted by a compound endodomain, an optimal T-cell activation signal may require different proportions of different immunological signals.

Nucleic Acid

The present invention further provides a nucleic acid encoding the targeting component of the second aspect and a nucleic acid encoding a signalling component of the third aspect.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Nucleic Acid Construct

The present invention also provides a nucleic acid construct which encodes both the targeting component and the signalling component.

The nucleic acid construct may produce a polypeptide which comprises the targeting component and the signalling component joined by a cleavage site. The cleavage site may be self-cleaving, such that when the polypeptide is produced, it is immediately cleaved into the receptor component and the signalling component without the need for any external cleavage activity.

For example, the present invention provides a nucleic acid construct encoding a CAR signalling system according to the first aspect of the invention, wherein the nucleic acid sequence comprises the following structure:

A-X—B in which A and B are nucleic acid sequences encoding a targeting component or a signalling component as defined by the second and third aspects of the invention; and X is a nucleic acid sequence which encodes a cleavage site, such that A is cleaved from B after translation.

The cleavage site may be any sequence which enables the polypeptide comprising targeting component and the signalling component to become separated.

The term "cleavage" is used herein for convenience, but the cleavage site may cause the targeting component and the signalling component to separate into individual entities by a mechanism other than classical cleavage. For example, for the Foot-and-Mouth disease virus (FMDV) 2 A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode targeting component and the signalling component, causes the targeting component and the signalling component to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ/S (where '/' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the targeting component and the signalling component and the self-cleaving peptide is produced, it is immediately "cleaved" or separated into distinct and discrete first and second polypeptides without the need for any external cleavage activity.

The self-cleaving peptide may be a 2 A self-cleaving peptide from an aphtho- or a cardiovirus. The primary 2 A/2B cleavage of the aptho- and cardioviruses is mediated by 2 A "cleaving" at its own C-terminus. In apthoviruses, such as foot-and-mouth disease viruses (FMDV) and equine rhinitis A virus, the 2 A region is a short section of about 18 amino acids, which, together with the N-terminal residue of protein 2B (a conserved proline residue) represents an autonomous element capable of mediating "cleavage" at its own C-terminus (Donelly et al (2001) as above).

"2 A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above). The cleavage site may comprise one of these 2 A-like sequences, such as:

```
                              (SEQ ID No. 22)
YHADYYKQRLIHDVEMNPGP (SEQ ID No. 23)
HYAGYFADLLIHDIETNPGP (SEQ ID No. 24)
QCTNYALLKLAGDVESNPGP (SEQ ID No. 25)
ATNFSLLKQAGDVEENPGP (SEQ ID No. 26)
AARQMLLLLSGDVETNPGP (SEQ ID No. 27)
RAEGRGSLLTCGDVEENPGP (SEQ ID No. 28)
TRAEIEDELIRAGIESNPGP (SEQ ID No. 29)
TRAEIEDELIRADIESNPGP (SEQ ID No. 30)
AKFQIDKILISGDVELNPGP (SEQ ID No. 31)
SSIIRTKMLVSGDVEENPGP (SEQ ID No. 32)
CDAQRQKLLLSGDIEQNPGP (SEQ ID No. 33)
YPIDFGGFLVKADSEFNPGP
```

The cleavage site may comprise the 2 A-like sequence shown as SEQ ID No. 27 (RAEGRGSLLTCGDVEENPGP).

The present invention also provides a kit comprising a nucleic acid encoding the targeting component of the second aspect of the invention, and/or a nucleic acid encoding a signalling component of the third aspect of the invention.

Vector

The present invention also provides a vector, or kit of vectors, which comprises one or more nucleic acid sequence(s)/construct (s) encoding a targeting component and/or signalling component of the invention. Such a vector may be used to introduce the nucleic acid sequence(s) into a host cell so that it expresses the targeting component and signalling component of the CAR system according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention also relates to a cell, such as an immune cell comprising the CAR system according to the first aspect of the invention.

The cell may comprise a nucleic acid or a vector of the present invention.

The cell may comprise a receptor component and a signalling component of the present invention.

The cell may comprise at least one targeting component of the present invention. For example the cell may comprise one, two, three, four, five, up to a plurality of targeting components of the present invention.

The cell may comprise at least one receptor component of the present invention. For example the cell may comprise one, two, three, four, five, up to a plurality of receptor components of the present invention.

T cell may be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+CD25+FoxP3+Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing the molecules of the CAR system according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing the molecules of the CAR system according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR cells are generated by introducing DNA or RNA coding for the targeting component and signalling component by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR system according to the first aspect of the invention, for example by treatment with an anti-CD3 monoclonal antibody.

The T or NK cell of the invention may be made by:
  (i) isolation of a T or NK cell-containing sample from a subject or other sources listed above; and
  (ii) transduction or transfection of the T or NK cells with one or more a nucleic acid sequence(s) encoding the targeting component and/or signalling component of the CAR system according to the second and third aspects of the invention.

The T or NK cells may then by purified, for example, selected on the basis of expression of the antigen-binding domain of the antigen-binding polypeptide.

The present invention also provides a kit which comprises a T or NK cell comprising the CAR system according to the first aspect of the invention.

Pharmaceutical Composition

The present invention also relates to a pharmaceutical composition containing a plurality of cells expressing the components of the CAR system of the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The present invention provides a CAR cell of the present invention for use in treating and/or preventing a disease.

The invention also relates to the use of a CAR cell of the present invention in the manufacture of a medicament for the treatment and/or prevention of a disease.

The disease to be treated and/or prevented by the methods of the present invention may be an infection, such as a viral infection.

The methods of the invention may also be for the control of pathogenic immune responses, for example in autoimmune diseases, allergies and graft-vs-host rejection.

The methods may be for the treatment of a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The CAR cells of the present invention may be capable of killing target cells, such as cancer cells. The target cell may be recognisable by expression of a TAA, for example the expression of a TAA provided above in Table 1.

The CAR cells and pharmaceutical compositions of present invention may be for use in the treatment and/or prevention of the diseases described above.

The CAR cells and pharmaceutical compositions of present invention may be for use in any of the methods described above.

The invention will now be further described by way of Examples, which are meant to serve to assist one of ordinary skill in the art in carrying out the invention and are not intended in any way to limit the scope of the invention.

EXAMPLES

Example 1—Production of ZipCARs

Figure 3:
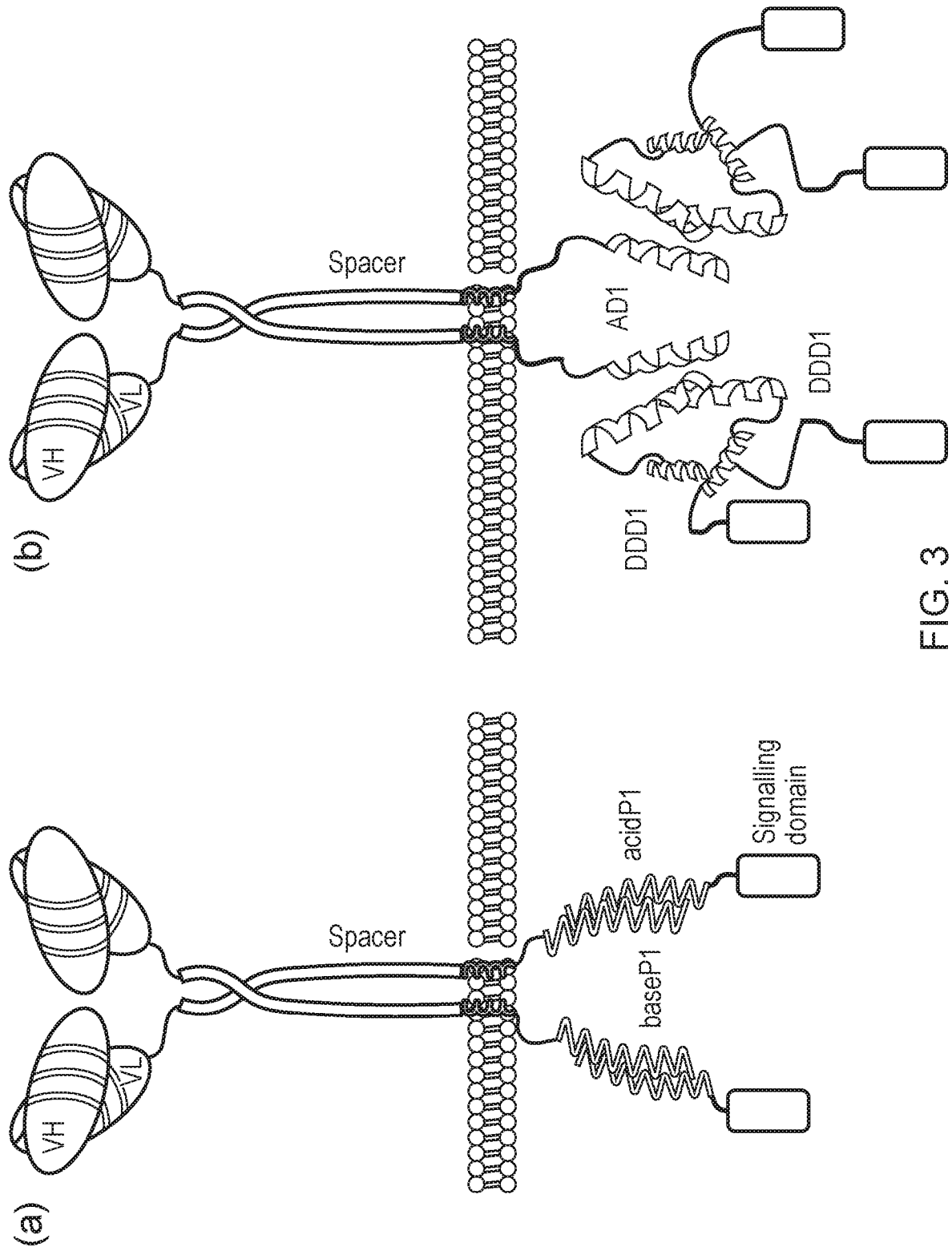
FIG. 3—(a) A Leucine zipper based zipCAR comprising Acid/Basic Leucine zippers. In this case, the homodimeric targeting component will recruit two signalling components. (b) A DDD1/AD1 based ZipCAR. In this case, since the DDD1/AD1 interaction is trimeric, the homodimeric targeting domain will recruit four signalling domains.

Two different zipCARs where constructed (see FIG. 3).
Leucine Zipper zipCAR

One zipCAR was constructed such that the targeting component recognized CD33 through an anti-CD33 scFv, and had an endodomain which comprised the Leucine zipper base, P1. This endodomain was linked to the transmembrane domain via a short intracellular linker sequence derived from CD4.

This targeting component was co-expressed with a signalling domain which comprised the leucine zipper acid P1 as a heterodimerization domain fused via a short serine-glycine linker to a signalling domain comprising the CD3-Zeta endodomain.

Figure 4:
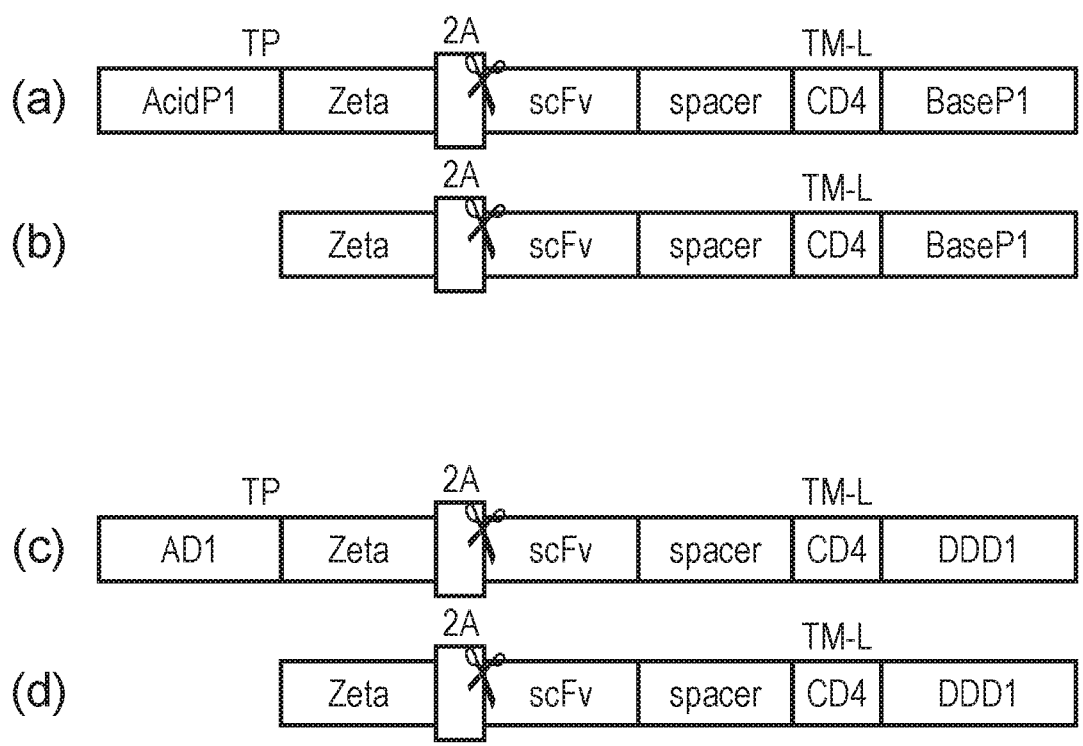
FIG. 4—zipCAR constructs. (a) A bicistronic construct to test an Acid/Base Leucine zipper zipCAR. (b) A control construct for the Leucine zipper zipCAR which is identical to construct (a) apart from the leucine zipper of the signalling component has been deleted. (c) A bicistronic construct to test the DDD1/AD1 based zipCAR. (d) A control construct for the DDD1/AD1 zipCAR which is identical to construct (c) apart from deletion of the AD1 segment from the signalling component.

Both components were co-expressed in the same retroviral vector using the self-cleaving FMD-2 A peptide (see FIG. 4).
DDD1/AD1 zipCAR The DDD1/AD1 zipCAR was constructed in an analogous fashion to the leucine zipper zipCAR. The endodomain of the targeting component comprised DDD1 and the signalling component was a fusion between AD1 and the CD3-Zeta endodomain (see FIG. 4).

For each zipCAR, the targeting component and signalling component are independent of each other following initial translation and self-cleavage by the FMD-2 A peptide. The targeting component is diverted to the cell surface via its signal peptide and anchored in the membrane via its transmembrane domain, whilst the signalling component remains in solution in the cytosol. The two components then associate via their respective heterodimerization domains.

Control constructs were generated for each zipCAR system. These were identical to the corresponding zipCAR constructs except that the heterodimerization domains of the signalling components were deleted (see FIG. 4). Hence, no intracellular association could occur.

The amino acid sequence of each of the described constructs is shown in FIG. 11.

Figure 5:
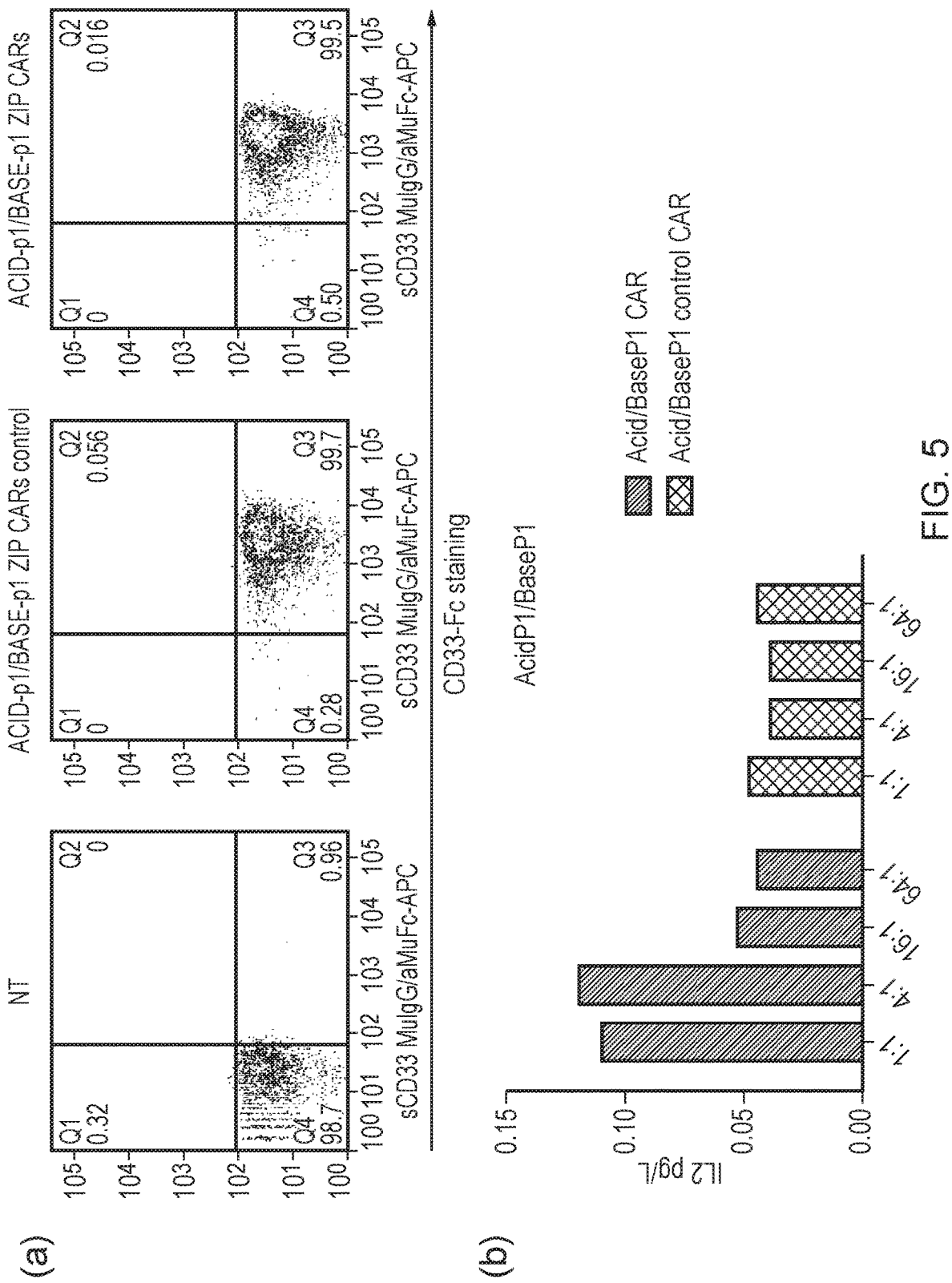
FIG. 5—Expression and function of the Acid/Base Leucine Zipper ZipCAR. (a) Expression of a non-transduced BW5 cell line, control leucine zipper zipCAR, and leucine zipper zipCAR is shown as staining of BW5 cells with recombinant CD33-Fc. (b) IL2 release of leucine zipper zipCAR and control leucine zipper zipCAR in response to cognate antigen at different effector to target ratios.
Figure 6:
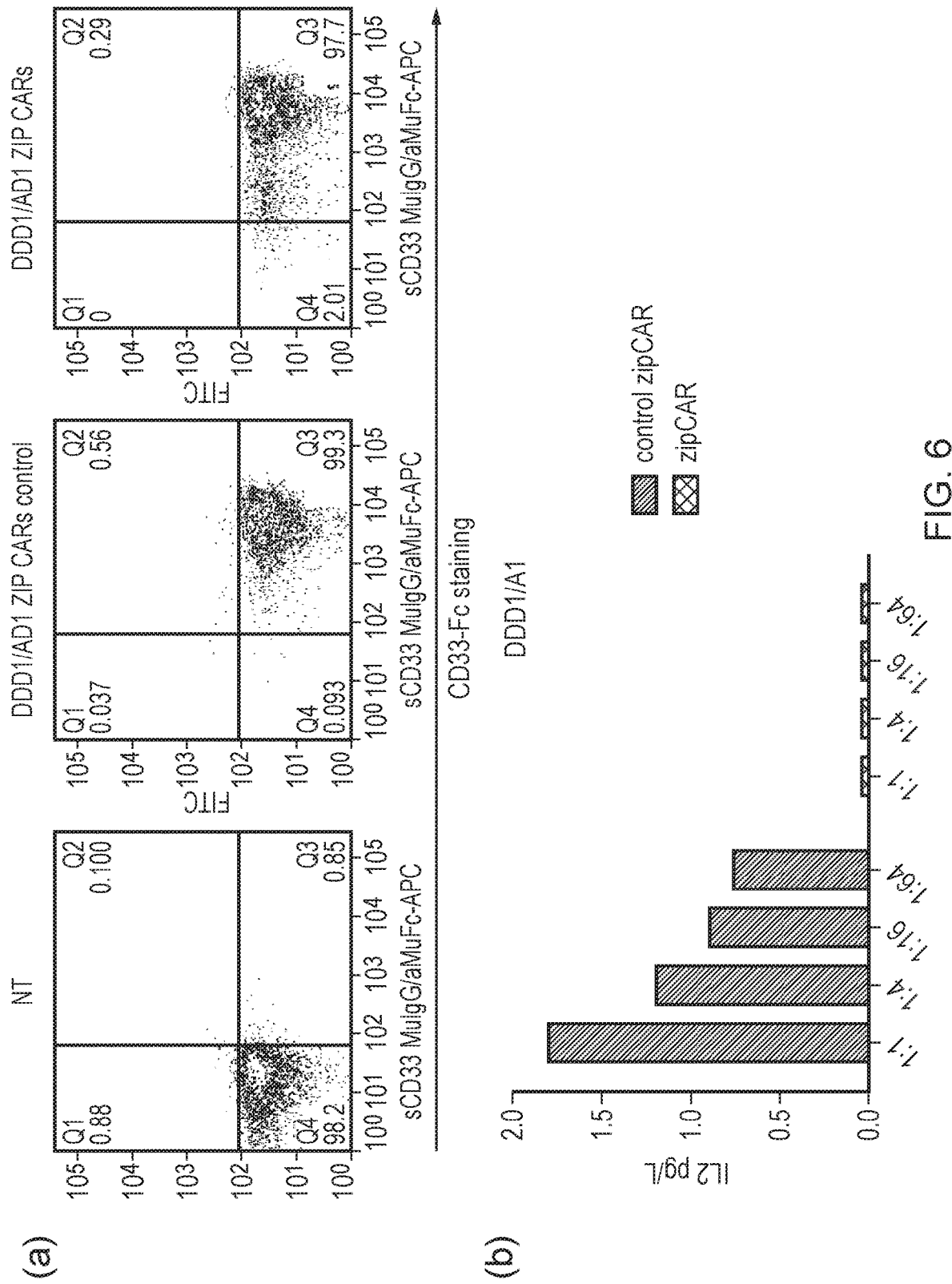
FIG. 6—Expression and function of the DDD1/AD1 ZipCAR. (a) Expression of a non-transduced BW5 cell line, control leucine zipper zipCAR, and leucine zipper zipCAR is shown as staining of BW5 cells with recombinant CD33-Fc. (b) IL2 release of DDD1/AD1 zipCAR and control DDD1/AD1 zipCAR in response to cognate antigen at different effector to target ratios.

The murine T-cell line BW5 was transduced with each zipCAR and respective control constructs. Expression of the CAR targeting domain could be detected by staining the T-cells with recombinant CD33-Fc fusion, staining with an appropriate secondary antibody and analysing the T-cells by flow cytometry (see FIGS. 5 and 6).

The T-cells were then challenged with beads coated with the cognate antigen (CD33) at different ratios of beads to T-cells. IL-2 release was measured after this antigen challenge. ZipCARs responded to the antigen while control constructs did not (see FIGS. 5 and 6).

Example 2—Production of SuperCAR ZipCARs

A DDD1/AD1 ZipCAR was constructed, in which the targeting component comprised an scFv against CD19, an IgGFc spacer, and eight heterodimerisation domains (FIG. 12). The targeting component was tested in combination with various different signalling components having 0, 1, 2 or 3 copies of the TCR zeta signalling domain. As DD1 binds AD1 in a 2:1 stoichiometry, these signalling domains give 0, 16, 32 and 48 copies of the TCR zeta domain respectively for each 8-heterodimerization-domain targeting component. As a control, an equivalent classical non-Zip-CAR format CAR was constructed, having two copies of TCR zeta (FIG. 12: IgG_Zeta).

The murine T-cell line BW5 was transduced with each zipCAR and the control construct and challenged with SupT1 cells expressing the cognate antigen (CD19) at different concentrations: low, mid and high. These SupT1 cells were engineered to express CD19 at different levels by the use of suboptimal signal peptides and/or the introduction of cytoplasmic retention motifs derived from Tyrp-1 (inserted proximal to the membrane) or glycoprotein E3-19 k from adenovirus (inserted on the C-terminus). IL-2 release was measured after antigen challenge.

Figure 13:
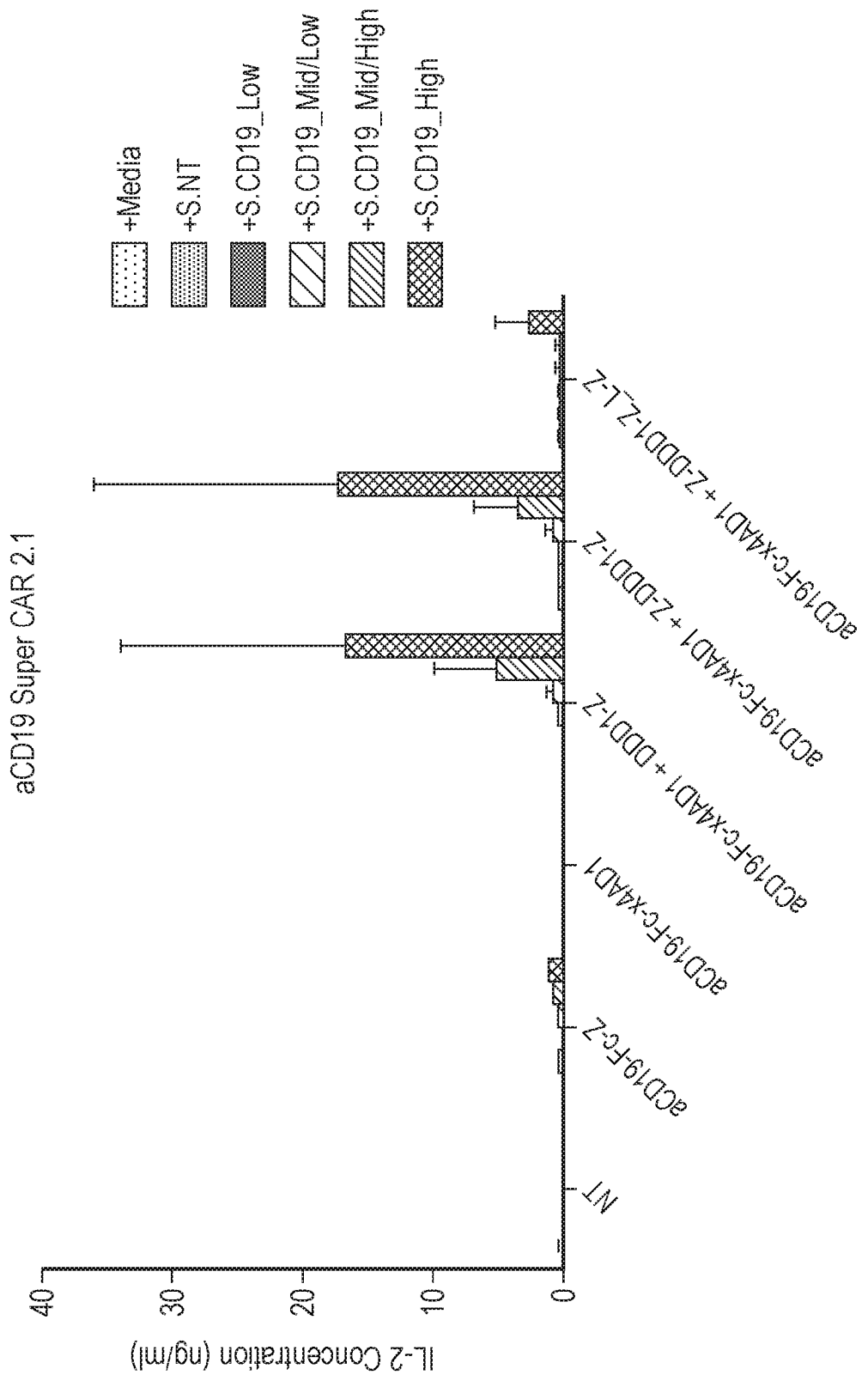
FIG. 13—IL2 release of DDD1/AD1 superCAR ZipCAR shown in FIG. 12 with various signalling components in response to cognate antigen at different levels of target antigen expression

The results are shown in FIG. 13. It was found that superCAR ZipCARs comprising 16 or 32 copies of TCR zeta per targeting component (IgGx4AD1+DDD1-Z and IgGx4AD1+Z-DDD1-Z respectively) gave a greater response to antigen than the equivalent classical CAR comprising two copies of TCR zeta per molecule.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

The invention claimed is:

1. A chimeric antigen-receptor (CAR) signalling system comprising;
   (i) a targeting component comprising an antigen-binding domain, a transmembrane domain and a first heterodimerization domain; and
   (ii) a soluble intracellular signalling component that localizes to the cytoplasm when expressed in a cell, comprising a signalling domain and a second heterodimerization domain;
   wherein the targeting component and the intracellular signalling component are separate molecules; and
   wherein spontaneous heterodimerization between the first and second heterodimerization domains causes the targeting component and signalling component to form a functional CAR complex.

2. The CAR signalling system according to claim 1, wherein the first and second heterodimerization domains comprise leucine zipper domains.

3. The CAR signalling system according to claim 1, wherein the first and second heterodimerization domains comprise DDD1 and AD1 domains.

4. The CAR signalling system according to claim 1, wherein the first and second heterodimerization domains comprise Barnase and Barstar domains.

5. The CAR signalling system according to claim 1, wherein the first and second heterodimerization domains comprise human pancreatic RNAse and S-peptide domains.

6. A cell which comprises a CAR signalling system according to claim 1.

7. The cell according to claim 6, which is a T cell or NK cell.

8. A pharmaceutical composition comprising a plurality of cells according to claim 6.

9. A method for treating or preventing a disease, comprising the step of administering a pharmaceutical composition comprising a plurality of T cells or NK cells which comprise a CAR signalling system according to claim 1 to a subject.

10. The method according to claim 9, comprising the steps of:
    (i) isolation of a T cell or NK cell containing sample from a subject;
    (ii) transduction or transfection of the T cells or NK cells with a nucleic acid construct or a vector comprising a nucleic acid construct encoding a CAR signaling system, wherein the chimeric antigen-receptor (CAR) signalling system comprises (a) a targeting component comprising an antigen-binding domain, a transmembrane domain and a first heterodimerization domain and (b) a soluble intracellular signalling component that localizes to the cytoplasm when expressed in a cell, comprising a signalling domain and a second heterodimerization domain, wherein the targeting component and the intracellular signalling component are separate molecules; and spontaneous heterodimerization between the first and second heterodimerization domains causes the targeting component and signalling component to form a functional CAR complex, and wherein the nucleic acid construct comprises the following structure

A-X B in which A is a nucleic acid sequences encoding a targeting component and B is a nucleic acid sequence encoding a signalling component, and X is a nucleic acid sequence which encodes a cleavage site, such that A is cleaved from B after translation; and (iii) administering the T cells or NK cells from (ii) in a pharmaceutical composition to the subject.

11. The method according to claim 9, wherein the disease is cancer.

* * * * *